(12) United States Patent
Hallowell et al.

(10) Patent No.: US 8,602,789 B2
(45) Date of Patent: Dec. 10, 2013

(54) COGNITIVE AND LINGUISTIC ASSESSMENT USING EYE TRACKING

(75) Inventors: Brooke Hallowell, Millfield, OH (US); Hans Kruse, Athens, OH (US)

(73) Assignee: Ohio University, Athens, OH (US)

( * ) Notice: Subject to any disclaimer, the term of this patent is extended or adjusted under 35 U.S.C. 154(b) by 474 days.

(21) Appl. No.: 12/579,154

(22) Filed: Oct. 14, 2009

(65) Prior Publication Data

US 2010/0092929 A1 Apr. 15, 2010

Related U.S. Application Data

(60) Provisional application No. 61/105,132, filed on Oct. 14, 2008.

(51) Int. Cl.
*G09B 5/00* (2006.01)
*A61B 5/16* (2006.01)
*A61B 5/00* (2006.01)

(52) U.S. Cl.
USPC ............ 434/167; 434/178; 600/300; 600/558

(58) Field of Classification Search
USPC ......... 434/155, 156, 159, 167, 176, 180, 184, 434/262, 56, 169, 178, 179, 350; 600/558, 600/559; 351/238
See application file for complete search history.

(56) References Cited

U.S. PATENT DOCUMENTS

| | | | |
|---|---|---|---|
| 4,332,566 A * | 6/1982 | Mazeski et al. | 434/178 |
| 5,103,408 A | 4/1992 | Greenberg et al. | |
| 2001/0046659 A1* | 11/2001 | Oster | 434/178 |
| 2003/0181793 A1 | 9/2003 | Buschke | |
| 2006/0178597 A1 | 8/2006 | Fujimaki et al. | |
| 2007/0066916 A1* | 3/2007 | Lemos | 600/558 |
| 2007/0166675 A1 | 7/2007 | Atkins et al. | |
| 2007/0218439 A1* | 9/2007 | Delahunt et al. | 434/236 |
| 2008/0287821 A1* | 11/2008 | Jung et al. | 600/544 |
| 2009/0130640 A1* | 5/2009 | Hardy et al. | 434/236 |
| 2009/0312668 A1* | 12/2009 | Leuthardt et al. | 600/558 |
| 2011/0027765 A1* | 2/2011 | Nader | 434/236 |

OTHER PUBLICATIONS

Hallowell, Brooke; A New Way of Looking at Auditory Linguistic Comprehension; Current Oculometer Research; magazine; 1999; pp. 287-291; Plenum Press; New York.

Hallowell, Brooke et al.: Tracking Eye Movements to Study Cognition and Communication; The ASHA Leader; magazine; Nov. 16, 2004; pp. 4-5 and 22-25.

Hallowell, Brooke et al.; Using Eye Movement Responses to Index Auditory Comprehension: An Adaptation of the Revised Token Test; Aphasiology; magazine; 2002; vol. 16 (4/5/6); pp. 587-594; 2002 Psychology Press Ltd.

(Continued)

*Primary Examiner* — Robert J Utama
*Assistant Examiner* — Sadaruz Zaman
(74) *Attorney, Agent, or Firm* — Jason H. Foster; Kremblas & Foster

(57) ABSTRACT

Methods for assessing cognitive and linguistic abilities by tracking and recording the eye movements of a patient in response to predetermined verbal and visual stimuli. The methods incorporate conventional eye-tracking technology to acquire eye-fixation location and duration measures for testing linguistic comprehension, working memory, attention allocation, and the effect of semantic associative priming. Visual stimuli presented in the methods are carefully designed to reduce visually distracting features. Verbal stimuli are carefully designed to control for numerous linguistic features.

50 Claims, 14 Drawing Sheets

(56) References Cited

OTHER PUBLICATIONS

Heuer, Sabine; A New Eye Tracking Method to Asses Attention Allocation in Individuals with and without Aphasia Using a Dual-task Paradigm; dissertation presented to faculty of College of Health and Human Services of Ohio University; Jun. 2009; pp. 1-156.

Heuer, Sabine et al.; Visual Attention in a Multiple-Choice Task: Influences of Image Characteristics with and without Presentation of a Verbal Stimulus; Aphasiology; magazine; 2008; vol. 23 (3); pp. 351-363; Psychology Press Ltd.

Heuer, Sabine et al.; An Evaluation of Multiple Choice Test Images for Comprehension Assessment in Aphasia; Asphasiology; magazine; 2007; vol. 21 (9); pp. 883-900; Psychology Press.

Ivanova, Maria; Addressing Confounding Factors in the Study of Working Memory in Aphasia: Empirical Evaluation of Modified Tasks and Measures; dissertation presented to faculty of College of Health and Human Services of Ohio University; Jun. 2009; pp. 1-222.

Katz, Richard C. et al.; A Multinational Comparison of Aphasia Management Practices; International Journal of Language and Communication Disorders; 2000; vol. 35. No. 2; pp. 303-314.

Odekar, Anshula et al.; Validity of Eye Movement Methods and Indices for Capturing Semantic (Associative) Priming Effects; Journal of Speech, Language and Hearing Research; Feb. 2009; vol. 52; pp. 31-48; American Speech-Language-Hearing Association.

Hallowell, Brooke; Using Eye Movement Responses as an Index of Linguistic Comprehension; Ph.D. Thesis submitted to the Graduate College of The University of Iowa; Dec. 1991; pp. 1-135.

Manor, Barry R. et al.; Defining the Temporal Threshold for Ocular Fixation in Free-Viewing Visuocognitive Tasks; Journal of Neuroscience Methods; 2003, pp. 85-93; vol. 128.

\* cited by examiner

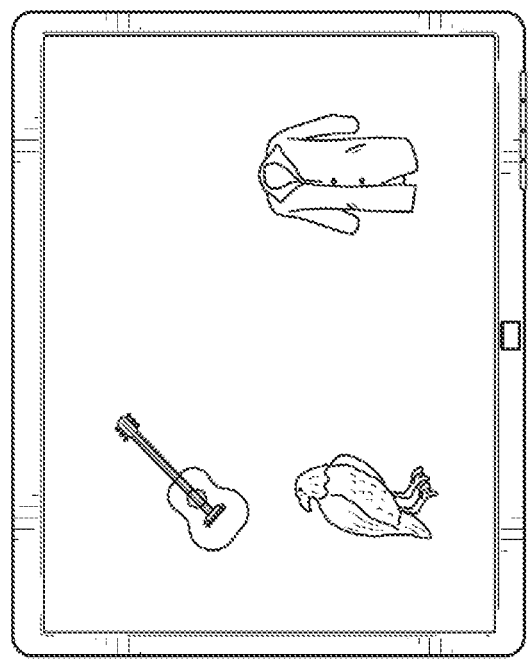
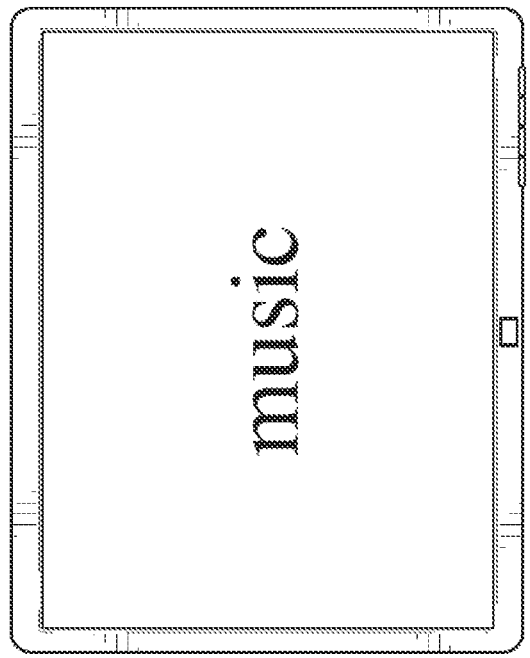
FIG. 7

CHARACTERISTICS OF SIMPLE AND COMPLEX SENTENCES

| GRAMMATICAL CHARACTERISTICS | NUMBER OF WORDS | NUMBER OF SYLLABLES | NUMBER OF VERBS | NUMBER OF PRE-POSITIONS | CENTER EMBEDDED PRE-POSITIONAL PHRASE |
|---|---|---|---|---|---|
| SIMPLE SENTENCE | | | | | |
| THE GREEN CIRCLE IS BY THE RED SQUARE | 8 | 9 | 1 | 1 | NO |
| COMPLEX SENTENCE | | | | | |
| THE CIRCLE NEXT TO THE RED SQUARE IS GREEN | 9 | 10 | 1 | 1 | YES |

FIG. 12

COGNITIVE AND LINGUISTIC ASSESSMENT USING EYE TRACKING

CROSS-REFERENCES TO RELATED APPLICATIONS

This application claims the benefit of U.S. Provisional Application No. 61/105,132filed Oct. 14,2008,which is incorporated herein by reference.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates generally to the field of cognitive and linguistic assessment methods and relates more particularly to methods for assessing cognitive and linguistic abilities by tracking the eye movements of a patient in response to pre-determined verbal and visual stimuli.

2. Description of the Related Art

Cognitive and linguistic abilities in individuals can be assessed and studied using a variety of well-known constructs, such as through testing of linguistic comprehension, semantic associative priming, working memory, and attention. As applied to individuals with neurological disorders, however, traditional clinical and research measures associated with such constructs are fraught with methodological limitations and "confounds," thus reducing the validity and generalization of findings. "Confounds" are factors that threaten assessment validity and that may be controlled through methodological design of tasks and associated performance measures, but not necessarily through randomization, restriction, matching, stratification or multivariate modeling (i.e., standard means of controlling confounding in epidemiological research).

Confounds associated with traditional methods for testing linguistic comprehension, semantic associative priming, working memory, and attention are especially prevalent in the evaluation of neurologically impaired patients who have concomitant motor and speech deficits, as is the case with many individuals who suffer from aphasia. Aphasia is an acquired neurogenic communication disorder that typically results from lesions to the language-relevant areas of the temporal and parietal cortex of the brain and the neural pathways between them, sometimes caused by a stroke, traumatic brain injury, or progressive neurological disease, e.g., Alzheimer's or Parkinson's disease. Aphasia can affect speaking, auditory comprehension, reading, and writing and can result in a number of nonlinguistic impairments. Aphasia is not a sensory deficit, general intellectual deficit, or psychiatric disorder.

Motor and speech deficits that often result from neurological disorders like aphasia can severely impede an individual's ability to provide necessary responses to test stimuli, such as by pointing, speaking, or manipulating a computer mouse or joystick when confronted with traditional cognitive and linguistic assessment tasks. A detailed discussion of each of the four assessment constructs mentioned above (i.e., linguistic comprehension, semantic associative priming, working memory, and attention) will now be presented, with particular attention given to traditional implementation of such constructs for evaluating neurologically impaired patients and related confounds. It should be noted that many of the concepts that are discussed under each of the following sections, including, but not limited to discussions of response requirements, ecological validity, instruction comprehension, offline measures, and memory constraints, represent ideas and features that are common to all of the constructs discussed below, and are therefore not limited to only those sections in which they appear.

I. Linguistic Comprehension

Distinguishing competence from performance may be problematic when appraising communication deficits in patients with neurological impairments. Motoric and perceptual deficits can be confounding factors when traditional linguistic comprehension test items requiring overt verbal, gestural, or graphic responses are administered. Thus, incorrect responses or failure to respond on traditional tests of linguistic comprehension do not necessarily indicate a failure to comprehend. Deficits in linguistic competence, therefore, may be overestimated. As a practical matter, knowing how much a person understands when listening to others speak is essential for appropriate treatment, socialization, and major life decisions related to living arrangements, financial management, legal status, and potential for return to work, educational, and leisure activities.

A. Traditional Comprehension Tasks

Most people who have had a stroke or brain injury have motor, perceptual, and other deficits that may impair their ability to respond, or to respond correctly, when traditional tests of linguistic comprehension are administered. Traditional means of comprehension assessment include story retell tasks, questions in spontaneous conversation, questions about written or spoken content presented to the patient, commands, and multiple-choice tasks which are briefly described here:

Story retell tasks: Patients are told a story and asked to retell it. If they are able to retell the basic elements of the story, this indicates that they understood the story. This task has an inherent confound of relying on short-term memory skills that may or may not interfere with actual linguistic comprehension. The longer the story to be retold, the more a person's memory is taxed prior to the moment when he or she begins to respond. Another critical confound is reliance on speech or writing. Many people who have a brain injury that affects communication have disorders of speech that may prevent them from retelling a story—or writing it—even when they have correctly understood it. To accurately assess comprehension, one must rule out the possible response failures or inconsistencies due to impaired speech, writing and memory.

Questions: The clinician asks a question (or shows a printed question to be read) and the patient answers it. If the response is appropriate, one assumes the patient understood the question. Reliance on speech or writing is a critical confound for many patients.

Commands: Clinicians present commands of increasing length and complexity and patients are instructed to carry out the commands. Examples of such commands are: Point to your nose; Point to the door and then to the window; Pick up the pen and put it on the book, then hand me the eraser. Critical confounds in such tasks are possible neuromuscular innervation problems limiting the required motor responses and also deficits in motor programming that may interfere with the planning and sequencing of required bodily movements even when people understand the commands.

Multiple-choice tasks: Clinicians present a set of images and give patients a verbal stimulus. The patient is to point to the image that best corresponds to the verbal stimulus. Neuromuscular innervation problems and deficits in motor programming are inherent confounds. Also, it is critical to control for a variety of potential visual deficits that may impair performance on such tasks; many clinicians do not assess or control for such deficits.

B. Confounding Factors

When means such as those described above are implemented to assess comprehension and other cognitive-linguistic deficits in patients, there are many potential confounds. These include comprehension of instructions, memory, motor programming and neuromuscular abilities required for responding, and problems associated with using off-line measures (those gathered after a task is completed) as opposed to on-line measures (those occurring while a person is engaged in a task). The existence and severity of deficits in many patients are often inaccurately estimated by experimental data, test results and clinical judgment, as well as by the impressions of patients' caregivers and significant others.

II. Semantic Associative Priming

Priming is a change in the speed or accuracy of a response that occurs as a consequence of a prior exposure to a semantically or phonologically related or unrelated stimulus. Priming paradigms have received considerable attention as a means to investigate the nature of language organization and processing. The various experimental variables in priming research include the nature of the relationship between prime and target, order of presentation of prime and target (direct forward and backward priming vs. mediated priming), format of presentation of prime and target (orthographic or picture stimuli; same format or cross-format), modality of presentation of prime and target, and temporal parameters such as interstimulus interval and prime duration.

Lexical decision and naming tasks have typically been used in studies of priming effects in varied modalities. In these tasks, participants are required to understand instructions, use verbal or motor responses, and/or engage in metalinguistic decisions (such as those required for lexical decision) that may be considered unnatural.

Lexical decision tasks have been used most commonly in the study of priming effects. This task involves classification of spoken or written words or non-words using overt physical (pressing buttons) or verbal ("word" or "non-word") responses. The dependent variables usually include response latency and accuracy of classification. Response latency is a particularly relevant measure for individuals with normal language for whom accuracy of responses is typically high. Although the lexical decision task is easy to use and offers a convenient means to measure priming effects, it poses a number of methodological problems in priming studies that are intended to investigate lexical organization and access. Many of the effects found in the word recognition literature, such as the word frequency effect, are heightened in the lexical decision task compared with the naming and category verification task, which suggests the role of variables such as familiarity with the letter strings and their meaningfulness (post-lexical access variables) in decision making. Lupker (1984) found pure non-associative semantic priming, which represents the overlap in meaning of two words, only in the lexical decision task and not in the naming task. Pure non-associative semantic relatedness represents pairs of words that are not associated with each other in terms of how frequently they occur together in text or spoken language. On the other hand, Lorch, Balota, and Stamm (1986) showed that large inhibition effects observed in the lexical decision task, when target words were preceded by unrelated primes, were not seen for the naming task. The authors interpreted these findings to suggest that the lexical decision task is a result of processes operating after recognition. Many authors believe that lexical decision tasks represent an unnatural response, because normal language processing seldom requires word and non-word classifications and requires that participants make metalinguistic judgments regarding targets. This task, therefore, has reduced ecological validity. Lexical decision requires overt physical (button pressing) or verbal responses (oral) from participants. These task-based influences on reaction times and latency of responses pose potential confounds in studying lexical access, as they reflect speech and limb-motor processes in addition to lexical processes. In light of these issues, it is possible that compromised validity of lexical decision tasks in studying priming effects may lead authors to develop inaccurate inferences regarding lexical access processes.

The naming paradigm has also been widely used to investigate priming effects. In the naming task, pictures are to be named aloud as quickly as possible by the participants. This task is sometimes termed "pronunciation" in visual word recognition. The dependent variables typically used are response latency and error rate. The naming task has several advantages over the lexical decision task. First, it is a relatively natural response and does not require metalinguistic judgments on the part of participants. Additionally, it may be a better reflection of the word recognition process, as it does not involve complex decision making that is required in lexical decision.

Although naming averts some of the shortcomings of the lexical decision task, its utility in studying word recognition, especially in the visual domain, has been questioned. Balota and Chumbley (1985) attempted to isolate the effects of word frequency on lexical access from its effects on production stages of naming by having participants name words only after a cue was provided with a certain delay. Word frequency effects on naming latencies emerged even for the 400-ms delay condition and were only slightly less (41-ms difference between naming of high vs. low frequency words) than the frequency effects obtained for the normal naming condition without any induced delays (58 milliseconds). The participants showed frequency effects for delay conditions spanning as long as 2,900 milliseconds when participants' rehearsals of the presented words during the delay were disrupted by use of auditory distracters. The authors concluded that presence of frequency effects long after the time required for lexical access has elapsed indicates that frequency effects occur during the post-lexical production stage in addition to the lexical access stage. According to Paap, McDonald, Schvaneveldt, and Noel (1987), orthographically regular non-words can be "pronounced" directly by means of grapheme-phoneme correspondences. Luce has expressed similar concerns regarding the naming paradigm in auditory word recognition, stating that phonological components of presented words may be directly coded into articulatory signals without necessitating lexical mediation. These studies demonstrate that naming latencies may not truly reflect lexical access or assess priming effects. As investigations of priming effects continue to be of importance in theory-based studies of language processing for individuals with normal language and individuals with linguistic deficits, the development and validation of alternative methods for the study of priming that reduce the above-mentioned potential sources of confound are needed.

III. Attention Allocation

The term "attention" has been used in the literature interchangeably with the terms "processing resources," "capacity," and "cognitive effort." Attention is a set of functions that allows individuals to respond flexibly to task and environmental demands. Attention is a limited resource that can only be allocated to a finite number of tasks. Attention allocation efficiency depends on each individual's meta-analytical skills to assess task demands.

Individuals with aphasia frequently have not only language impairment but also difficulties properly allocating attention resources required for language processing. This limitation of attention is generally considered an important contributor to deficits in language comprehension and formulation. With an increase in task demands, more attention resources are required. If task demands exceed existing resources, deficits in language comprehension occur or become more severe.

A. Importance of Attention in Language Processing for Individuals with and without Language Impairment Attention resources are limited in all individuals, not only in individuals with aphasia. However, individuals free of neurogenic impairment may generally be able to compensate better for a shortage of attention. For instance, they have been shown to better utilize cues such as information about the to-be-expected probability of occurrence of a target stimulus. Individuals free of neurogenic impairments also tend to orient attention faster, more accurately and more flexibly than individuals with aphasia. Murray et al. (1997) found that participants without aphasia were better able to adapt to increased task demands by responding more slowly but maintaining high accuracy levels compared to individuals with mild to moderate aphasia. However, Blackwell and Bates (1995) demonstrated that individuals free of neurogenic impairments perform similarly to individuals with aphasia on a semantic judgment task when the task demands exceed the participants' attention resources in a dual-task experiment. Understanding how attention is allocated during language comprehension is important when trying to understand normal and impaired language processing.

B. Clinical Importance of Attention in Language Processing in Individuals with Language Impairment Understanding attention impairment in individuals with aphasia is important in terms of theoretical implications as well as implications for language assessment and treatment. Attention deficits, when not recognized, may lead to invalid assessment of language skills. It is therefore crucial for clinicians to be alert to different types of attention impairments, assess attention deficits in addition to language impairments, and create appropriate treatment plans involving attention. Few studies to date explore treatment of attention deficits in individuals with aphasia. Murray (2004) reviewed studies of attention treatment in individuals with aphasia and concluded that these few studies require replication and often lack strong research designs. Attention deficits may negatively affect not only language comprehension but also learning in individuals with aphasia. Therefore, it is important to understand the interaction of attention and language comprehension in individuals with neurogenic language impairments.

C. Theoretical Foundations

An efficiently functioning attention system is crucial for all cognitive processes. Attention is required in order to perceive information consciously. Without intact attention we would be unable to filter adequately the constant stream of information in our environment. Attention is also required for any higher cognitive processes involving working memory or executive functions. Connor, MacKay, and White (2000) pointed out that attention capacity limitations may lead to insufficient inhibition of task-irrelevant information in working memory processes, thus slowing the working memory system and limiting storage and processing activities. Several working memory models include a component that surveys attention allocation to its subsystems according to task demands. For instance, the central executive (CE) in Baddeley's working memory model allocates resources to the phonological loop and the visuospatial sketchpad. The phonological loop and the visuospatial sketchpad are responsible for processing and maintenance of auditory and visual information. The CE itself requires cognitive resources to evaluate task demands. Similarly, the supervisory attentional system (SAS) proposed by Shallice and Burgess (1993) assigns attention resources or inhibits activation of resources in the form of action schema depending on task demands. Across all of the models, attention is viewed as a global resource that fuels cognitive processes, crucial for all components of cognition, including language processes.

D. Assumptions About Attention

Different models of attention and cognitive models that involve attention as a component emphasize different aspects of attention. Some models emphasize the organization of functions of attention in networks. Mirsky, Anthony, Duncan, Ahearn, and Kellam (1991) and Mirsky, Pascualvaca, Duncan, and French (1999) proposed the following functions: focused attention, sustained attention, and attention shifting. Focused and sustained attention require that one be able to concentrate on one piece of information while inhibiting unnecessary information. Sustained attention requires the ability to scan information and respond consistently to a set of target stimuli. Shifting attention requires the ability to identify flexibly changing target stimuli and to inhibit non-target information accordingly. O'Donnell (2002) described similar functions of attention, including not only focused and sustained attention but also divided attention, which requires the ability to allocate attention to two tasks simultaneously. Some models emphasize the processes in which attention is involved. For instance, the Central Executive (CE) in Baddeley and Hitch's (1974) model of working memory is a component that allocates resources to its subsystems. Most of these models share basic assumptions about attention.

One shared assumption across models is that attention is a set of functions that allows us to respond differentially to information in our environment. For instance, in the working memory model originally proposed by Baddeley and Hitch, the CE is a structure that allocates attention to storage and processing of information. Encoding of auditory information requires continuous sub-vocal rehearsal. Just and Carpenter's (1992) working memory model of storage and processing are both fueled by "activation" or attention. Engle, Kane, and Tuholski (1999) stated that working memory is responsible for maintaining relevant information while inhibiting distracter information. All of these processes (encoding, storage, maintenance, and inhibition) are considered functions of attention much as Mirsky et al. (1991) considered sustained, focused, and shifting attention to be essential functions of attention that are allocated flexibly depending on the environmental and task demands.

A second assumption is that attention is a limited resource that only can be allocated to a finite number of tasks. Attention is limited and is distributed flexibly according to processing needs. This resource is assumed to be distributed across its different functions. The amount of resources required depends on the task demands in terms of complexity, duration and difficulty. If a task is demanding enough, it may exhaust a limited resource pool. Demands may be increased in several ways. The required resources depend on the duration of the task, the distinctiveness of the target and non-target stimuli and the predictability of patterns in which the target stimuli appear. For instance, a task in which target stimuli occur only intermittently and are similar to non-target foils requires more resources than a task in which the listener knows when to expect a certain stimulus to occur and in which target and non-target stimuli are clearly differentiated. A divided attention task, or dual task, is likely to require more resources because two tasks have to be attended to at the same time as compared to only attending to a single task. If the resource capacity is exceeded, task performance decreases. Depending on the demands of the secondary task, performance on the primary task may deteriorate. Divided attention tasks are also referred to as "dual tasks" in the literature.

A third assumption is that attention allocation efficiency depends on meta-analytical skills that are not task dependent. The ability to evaluate task demands prior to and during processing is crucial to the use of compensatory strategies if needed. For instance, if tasks become more difficult, individuals may respond more slowly in order to maintain high accuracy rates. Murray, Robin and Rizzo, and Tseng et al. have pointed out that individuals with aphasia have difficulty making use of compensatory strategies and cues in order to improve their performance on linguistic and nonlinguistic tasks. Robin and Rizzo (1988) conducted a study examining the abilities of individuals with right and left hemisphere brain injuries to orient their attention toward auditory and visual stimuli after being cued toward the direction of expected target occurrence. On a computer screen an arrow was presented as a cue, pointing to the left, the right, or both directions. This cue was followed by a delay of 200 to 600 milliseconds and then a visual or auditory target stimulus. Orientation of attention was assessed in visual, auditory, and mixed modality conditions. Reaction time measures served as the dependent variable. The individuals with right and left hemisphere injuries overall had significantly longer reaction times than individuals in the control group. Results for individuals with aphasia showed no differences in reaction times with regard to valid, invalid, or neutral cues, indicating that they did not benefit from the cues.

Overall, individuals with aphasia exhibited the greatest impairment in the auditory modality. Results suggest that an overall deficit in attention orientation to auditory and visual stimuli might contribute to inefficient attention allocation required for language processing in individuals with aphasia. This deficit in orienting linguistic stimuli may affect the ability to process linguistic stimuli effectively, which may lead to comprehension deficits because the stimuli were not attended to in the first place.

Tseng et al. (1993) provides further evidence that meta-analytical skills influence attention allocation. They presented tasks with and without explicit instructions about the likelihood of occurrences of target stimuli to which individuals were asked to respond as quickly as possible. Individuals without aphasia made use of those instructions, as indicated by shorter reaction times and lower error rates, compared to performance when they were not given explicit instructions. Individuals with aphasia did not show any difference in performance between the tasks with and without instructions. Murray et al. (1997) conducted a study in which participants with and without aphasia were presented dual tasks containing a semantic judgment task and a tone discrimination task. The authors reported that individuals free of neurogenic impairment responded with slower reaction times but maintained accuracy levels despite increasing processing loads during dual-task performance while individuals with aphasia performed overall more poorly on linguistic and nonlinguistic tasks when task demands increased. These results indicate that individuals without aphasia were better able to analyze task demands and to alter their performance on the tasks with increased processing load while individuals with aphasia did not appear to modify their performance. Intact attention relies on sufficient attention allocation and capacity. Deficits in either one or both components of attention may lead to attention deficits.

E. Dual Tasks to Assess Attention in Individuals with and without Language Impairment Dual-task experiments have been used widely to support resource allocation models of attention addressing focused, sustained, and divided functions of attention. When two tasks are performed at the same time, decrements in performance of one task reflect the processing load imposed by the second task. Dual task paradigms have been used to explore the relationship between limited attention and language comprehension.

F. Dual Tasks to Assess Attention in Individuals with Aphasia

LaPointe and Erickson (1991) conducted a study to explore sustained auditory attention in individuals with aphasia. Six male individuals with aphasia due to a left cerebral vascular accident (CVA) and a mean post-onset time of 69.8 months, with severity ranging from mild to moderate as determined by the Porch Index of Communication Abilities participated in the study. Six male adults matched for age and education, free of a history of neurogenic impairments, served as the control group. Participants completed tasks in two conditions: an auditory vigilance task alone and an auditory vigilance task with a card sorting test. Participants listened to a list of monosyllabic English words and raised a hand when a target word occurred. Control participants had no difficulty with the dual task and performed the auditory sustained attention task similarly in isolation and in the dual task. Individuals with aphasia performed similarly to the control participants on the vigilance only task but more poorly on the auditory sustained attention task when presented with the card sorting task. The authors argued that auditory sustained attention is a crucial component of auditory comprehension because maintaining sustained attention to monitor auditory input is fundamental to understanding a message. The authors interpreted the results as supportive of the theory that resource allocation deficits caused by neurological damage underlie auditory comprehension impairments and variability of performance in individuals with aphasia. LaPointe and Erickson collected data only on accuracy, not on response time. Valuable insights about processing time comparing single and dual task performance might have yielded additional insights in that experiment. For instance, differences in performance between single and dual tasks in the control group might have been detected, supporting the notion that capacity limitations affect processing in the non-impaired population. Also, neither the participants' aphasia type nor lesion site was specified, despite the fact that type of aphasia is likely to play a role in their performance during the word recognition task. Words in the word lists were described as common English monosyllabic words, but no frequency ratings for the target words were given. Despite these methodological limitations, the study supports the hypothesis that reduced attention capacity or resource allocation can affect the performance on linguistic tasks in individuals with aphasia. The authors concluded that the nature of aphasia might be characterized by inefficient resource allocation in conjunction with linguistic deficits and not linguistic deficits alone.

Tseng et al. (1993) investigated attention allocation skills in nine individuals with aphasia and 18 controls in a dual-task experiment recording performance accuracy and reaction time. Participants listened to word lists that were presented audibly. They were instructed to identify semantic or phonetic targets during the single-task condition. During a dual-task condition, participants were asked to identify both semantic and phonetic targets. A semantic target was defined as a word that belonged to the semantic category of food items. A phonetic target was defined as a two-syllable word with the consonant /b/ in medial position. For half of the trials (240), participants were given instructions about the probability for detecting a semantic or phonetic target. For the remaining 240 trials participants were uninformed about the probability of target occurrence. The probability of occurrence of a phonetic or semantic target was modified at three levels: 0.2, 0.5 or 0.8. At the beginning of each experimental session, participants were asked to identify phonetic or semantic targets or both and were asked to press one of two buttons on a keyboard, labeled "yes" and "no" to indicate their response. Accuracy and reaction time were measured. Individuals without brain injury improved their performance through faster reaction times and lower error rates compared to individuals with aphasia. Individuals with aphasia did not make use of explicit instructions about the probability of occurrence of a particular target word in an auditory target detection task as indicated by significantly higher error rates. Further, individuals with aphasia performed better on the single semantic judgment task than in the dual tasks, indicating that they were able to perform the task in isolation but were unable to efficiently allocate attention during the dual-task condition. Results of this study indicate that impaired attention allocation abilities increase the performance deficits in individuals with aphasia when task demands exceed capacity resources. Participants with aphasia did not utilize information about the probability of targets, which indicates that they were unable to evaluate task demands efficiently. These performance deficits are said to be due not to linguistic impairments per se but rather due to an inefficient allocation of resources.

Murray et al. (1997) explored auditory-linguistic processes of individuals with mild aphasia in a dual-task paradigm under different attention conditions: in isolation, focused attention and divided attention. During the isolation condition only one of the tasks was administered. During the focused attention condition, two tasks were administered simultaneously, but the participants were asked to focus on one of the tasks.

During the divided attention condition participants were asked to distribute their attention evenly between the two tasks. Sixteen individuals with aphasia and eight control participants matched for age, estimated IQ, and education participated in the experiment. The individuals with aphasia each had a left-hemisphere stroke and all were at least six months post-onset. Severity was assessed with the Aphasia Diagnostic Profiles. Of the 16 participants 8 had a lesion anterior to the central gyrus and 8 had a lesion posterior to the central gyrus. There were no significant differences between these two subgroups with respect to severity, lexical retrieval, or auditory comprehension as assessed by the ADP. All participants engaged in a semantic judgment task. They had to determine whether a presented word belonged in a specific semantic category. The secondary task was either a tone discrimination task or a lexical decision task in which participants listened to word lists and were instructed to decide whether the word was a real word or a non-word. Individuals with aphasia displayed accuracy decrements in the focused attention condition compared to the task in isolation.

Controls did not perform less accurately during the focused attention condition compared to the task in isolation. That is, competing stimuli had a deteriorating effect on performance of individuals with aphasia. These results suggest that focused attention deficits may negatively affect accuracy.

During the dual-task attention condition the performance of individuals with aphasia was significantly poorer in accuracy and slower in speed compared to the control participants. All individuals exhibited lower accuracy and slower reaction times when the secondary task was a verbal task compared to a tone discrimination task. Aphasia severity did not correlate with the task performance expressed as the differences in accuracy between the isolation condition and divided attention condition and differences in reaction time during isolation compared to the divided attention condition. In other words, the discrepancies in performance between isolation and the divided attention conditions were not greater for individuals with more severe aphasia than for those with less severe aphasia. No differences in performance between participants with frontal damage and posterior damage were found. With eight participants in each group and heterogeneity of lesion sites, lesion extent, and heterogeneity of other variables such as months post onset, conclusions about associations of lesion site and possible attention deficits must be drawn with caution. Possibly, grouping participants by different criteria, such as by types of auditory comprehension deficits, classic aphasia subtypes, or a combination of factors related to site of lesion, might have permitted firmer conclusions about severity and performance.

King and Hux (1996) conducted a dual-task experiment to assess attention allocation of eight individuals with aphasia and eight individuals without neurological disorders on linguistic and nonlinguistic tasks. The control participants were matched for age, gender and education. Individuals with aphasia were 2 to 11 years post onset. Five individuals with aphasia had mild auditory comprehension and word-finding difficulty as indexed with the WAB and three had moderate to severe auditory comprehension impairment and telegraphic speech output. All participants passed a pure tone hearing screening and speech discrimination screening. Fifty images were chosen from the Snodgrass and Vanderwart collection (1980). They were black and white line drawings corresponding to one-syllable words. Twenty-five images were used for practice trials and 25 for actual testing. Auditory stimuli were recordings of a male and a female speaker saying the words corresponding to each image. During the single-task condition participants were presented with the word-picture pair and were required to answer the yes/no question "Does the word you hear match the picture you see?", or they were only presented with the auditory stimuli and were asked "Is the speaker a male?". During the dual-task condition, participants were presented with the word-picture matching stimuli and were asked "Does the word you hear match the picture you see and/or is the speaker a male?". Thus, only one response was required during the dual task; "yes" for picture-word match and male speaker, for picture-word match and female speaker, and for no picture-word match but male speaker. Participants were asked to respond with "no" when there was no picture-word match and speaker was female. Participants indicated their yes or no response using response buttons on a two-switch response box. In terms of accuracy, individuals with aphasia and individuals in the control group performed similarly in the single-task conditions. In the dual-task condition, participants with aphasia had a significantly lower accuracy rate compared to the control group. Results of response time measures were compared for only six of the eight individuals with aphasia. Data of two participants were excluded because of their poor performance in terms of accuracy. Overall, individuals with aphasia performed significantly more slowly than the control group. Further, for all participants in the control group and three of the six participants with aphasia, reaction times increased significantly with increases in task difficulty from the single gender recognition task to the picture-word matching task to the dual task. For the remaining participants with aphasia, reaction times for the picture-word matching task were slower than for dual-task processing. According to the authors, this may reflect the strategies that participants reported that they used during the dual task. Individuals with aphasia and seven control group members attended first to the gender component of the task and then to the picture-word matching task. When the speaker was male they could respond accurately with "yes" without having to attend to the picture-matching task. Participants had to attend to the picture-matching task only if the speaker was female. Nevertheless, when comparing linguistic and nonlinguistic single-task performance to dual-task performance, the longer reaction times of individuals with aphasia indicate reduced efficiency or limited attention allocation ability even when they maintained the same accuracy as controls. Significantly greater variability in reaction time measures was observed in individuals with aphasia compared to the control group. Although results of this study confirm the trend found in other dual-task studies, results must be considered with caution for several reasons. First, as the authors acknowledged, the number of participants was small as was the number of stimuli. Only 25 images were presented in each of the three attention tasks. Thus, there were as few as four stimulus items in a single category (5 match-male, 4 match-female, 4 no-match male, and 12 no-match female). Second, the use of parametric statistics in the analysis of results based on so little data is questionable. Third, participant descriptions lack sufficient detail in terms of site and extent of lesion. Fourth, as the authors pointed out, because only a single response was required during the dual task, participants only had to attend to one of the two tasks, which may have significantly influenced the results of the reaction time analysis as well as the analysis of accuracy.

G. Dual Tasks to Assess Attention in Language-Normal Adults

Several authors have studied the relationship between attention and language comprehension in individuals without neurogenic impairments using dual-task paradigms. Blackwell and Bates (1995) explored this relationship by having individuals without brain injury perform language tasks under conditions in which attention resources were stressed, causing the participants to perform similarly to individuals with language impairments. Blackwell and Bates showed that receptive agrammatism similar to that of Broca' s aphasia can be induced in individuals without neurogenic impairment when the load of cognitive processing is increased. One hundred and twelve undergraduate students participated in one of two conditions. One group was presented spoken sentences that they were instructed to judge for grammatical correctness by pressing a "good" or "bad" button. The sentence stimuli contained a variety of errors: transpositional, omission, and agreement errors. Participants were asked to make their judgments as fast as possible. A second group of participants listened to the same set of sentences. Prior to each sentence they were presented with a sequence of two, four, or six digits. The digits were presented visually on a computer screen one at a time. Immediately after the initial digit sequence, the sentence was presented audibly and participants were to give their grammatical judgments as fast as possible via pressing a "good" or "bad" button. Then, a sequence of digits appeared again on the computer screen and participants were instructed to judge by pressing the "good" or "bad" button according to whether the second sequence was identical to the first sequence. Accuracy and response time were measured. When detecting grammatical errors in the sentences with an increase in digits per sequence to remember, healthy adults performed more like individuals with Broca's aphasia would perform. That is, they more easily detected errors in syntax than morphological errors in grammatical judgment tasks. Thus, individuals with receptive agrammatism are more likely to detect transposition errors (e.g., "She walking is the dog") than omission errors (e.g., "She walking the dog") or agreement errors (e.g., "She are walking the dog"). Agreement errors were particularly difficult for the participants to detect while omission and transposition errors were detected easily even under a high cognitive load. The authors argued that the likelihood of detecting each error type is associated with the different processing load required to detect each type of error. Agreement errors required the most syntactic analysis, thus demanding the most effort, and are consequently the most vulnerable in the presence of a dual task where global resources are shared.

Granier, Robin, Shapiro, Peach, and Zimba (2000) conducted one of the few studies assessing attention demands online during an auditory comprehension task in adults without histories of neurogenic impairment. Different aspects of task demands, such as fast, initial, automatic processing (e.g., as assigning meaning to words during listening), and effortful processing, (e.g., sentence integration and interpretation immediately before answering yes-no questions), require different amounts of attention. Granier, et al. attempted to measure attention during fast, automatic, and effortful comprehension processes using a visuomotor tracking task. The authors stated that motor tracking is sensitive to changes in attention required during cognitive and linguistic processing. A dual task, with the primary motor tracking task and the secondary listening task, was implemented. They measured accuracy of visuomotor tracking performance while presenting sentences audibly to 19 healthy adult participants who were instructed to track a 1.5 inch horizontal bar that moved unpredictably up and down on a computer screen. The tracking occurred with a "tracker dot" attached to the participant's finger. Accuracy was measured by comparing the correspondence of the target bar and the tracker waveforms. While tracking the bar movement, participants listened to 150 sentences. Fifty of those were followed by yes-no comprehension questions and participants were asked to respond orally to those questions. Tracking measures were analyzed at different sentence locations: at the beginning (first 500 milliseconds) when the processing load was hypothesized to be relatively small; at the end of a sentence (last 500 milliseconds) when the processing load was hypothesized to be greater; during the gap after a question and immediately before the participant responded orally; and when processing load was hypothesized to be greatest. Tracking performance was reduced during processes in the gap and during the verbal response compared to the beginning and end of a sentence, indicating a greater processing load before and during question answering compared to when simply listening to a sentence. As the authors acknowledged, they were unable to conduct a more detailed analysis of participants' processing loads while listening to a sentence. For example, the number, size and placement of the probes did not allow a detailed analysis of the time course of changes in the mental workload associated with the different types of processing, such as activation of verb-argument structures or end-of-sentence integration. The authors pointed out that they would continue to analyze tracking performance with narrower sentence segments, hopefully leading to more precise recordings of changes in processing load. However, the authors emphasized that the decreased tracking performance (during processing in the gap between listening to the sentence and answering the question) is an indicator that the tracking task captures changes in processing load. The authors suggested that this difference in tracking performance supports the claim that tracking tasks are sensitive to changes in attention processing demands and that the use of dual-task paradigms to investigate low and high processing load demands in individuals with aphasia may help further study the role of resource capacity in aphasia. Better insight into resource allocation processes during language comprehension might be found when the stimulus sentences are better controlled in terms of length and complexity.

H. Summary: Individuals with Aphasia

Individuals with aphasia have been shown to exhibit difficulty allocating attention efficiently during dual-task performance compared to single-task performance and their shortage of capacity resources leads to greater deficits during dual-task performance compared to single-task performance.

I. Summary: Individuals without Aphasia

Individuals free of neurogenic impairment also have been shown to perform less accurately on dual tasks than on single tasks. Blackwell and Bates (1995) demonstrated that individuals free of neurogenic impairments perform similarly to individuals with aphasia on a semantic judgment task when the task demands exceed the participants' attention resources in a dual-task experiment. Thus, the dual-task paradigm appears to be a valid tool to assess changes in performance of language comprehension when attention demands are manipulated to exceed the participants' attention resources.

J. Challenges of Dual-Task Experiments

Although valuable insights have been gained from dual-task studies, there are challenges to dual-task designs that potentially affect validity of the results. Potential confounds are associated with the task demands associated not only with single and dual task conditions, but also with the processing of dual task instructions prior to the actual experiment, and response planning and execution of single and dual tasks.

K. Instructions

Instructions for dual tasks can be long, wordy, and complicated. Long and complex instructions may be confounding because people with language impairment might perform poorly due to a lack of comprehension of instructions and not necessarily because they do not have the resources to perform the actual tasks. Thus, insufficient language comprehension skills preclude individuals with severe language impairments from valid participation in dual task experiments. Additionally, short-term memory skills required to remember the instructions may be impaired in individuals with brain injury.

L. Single Task

Based on single-to-dual task performance comparisons, conclusions about the effects of increased task load on limited attention capacity are drawn. This is problematic because it is assumed that the increase of task load leads only to a quantitative increase in cognitive processes. Potential changes in quality of cognitive processes and the means by which these relate to attention resource capacity and allocation are not considered.

M. Offline Measures of Language Processing

Most measures of attention commonly require that participants respond with yes/no or true/false choices. Examples are target word recognition tasks, semantic category decision tasks, and semantic judgment tasks. Conclusions about attention allocation are drawn indirectly based on yes/no responses after the allocation process have been completed. Those measures are considered offline measures. However, the actual allocation process is not assessed. This is problematic because attention resources might not be stable from one moment to the next. Fluctuations in task resources cannot be recognized and thus are not considered when traditional offline measures are used.

N. Higher Cognitive Functions

Many attention tasks require intact processing, intact storage, and response planning in addition to allocation of attention. For instance, during a word recognition task participants are instructed to recognize a given word prior to responding with "yes" or "no." The task requires them to process the given word and to compare it to a mental target in working memory prior to the actual judgment. Inaccurate responses may be due to deficits in language processing, working memory (storage and processing), attention allocation, and response planning and execution. The task demands are often too complex to disentangle the actual linguistic deficit from underlying cognitive deficits of working memory and attention.

O. Task Response Requirements

All tasks require active response execution (e.g., through pushing buttons, tracking an object on the computer screen, or raising one's hand). These processes require adequate visual perception, eye-hand coordination, visual-spatial orientation, motor planning, and fine motor skills. These are areas of performance that are commonly affected by brain damage. For instance, CVA often leads to concomitant impairments of motor planning and execution manifested in hemiparesis, apraxia of speech, and limb apraxia. Further, motor response abilities are not commonly assessed prior to the experimental task; and poor performance is assumed to be a result of impaired attention allocation while in fact the performance may be due to poor motor control of the chosen response interface.

P. Response Confounds

When two tasks are presented simultaneously, both have to be responded to separately because it is not otherwise possible to assess attention allocation for the two tasks independently. Thus, one response has to be prioritized over the other and the performance on the secondary task might be confounded because, potentially, participants do not have the attention resources to complete the secondary task, or have difficulty shifting attention to the second task.

Q. Ecological Validity

A task's ecological validity refers to how much it entails a real-life activity in an everyday context. Dual tasks used in experimental designs can be unusual and compromise ecological validity because they are unlike tasks in which participants typically engage. For instance, motor tracking tasks, such as following a target on a computer screen with one's hand or the computer mouse, and unusual judgment tasks, such as judging pitch of tones, especially in combination with a language comprehension task, are not typical of everyday language processing tasks.

R. Summary of Potential Confounds

Potential confounds of traditional dual tasks include lack of ecological validity of allocating attention to two novel tasks, complex verbal instructions for potentially language impaired participants, and complex and challenging response requirements in addition to language comprehension, and a reliance on motor responses. Finally, offline measures such as yes/no responses during a sentence comprehension task require inferences about performance that online measures do not require.

IV. Working Memory

Working memory is broadly defined as "a multi-component system responsible for active maintenance of information in the face of ongoing processing and/or distraction". Deficits in working memory are a critical subset of nonlinguistic impairments in aphasia. Previous studies indicated that individuals with aphasia made more errors on working memory tasks compared to individuals without cognitive or neurological impairments. Also, an association between working memory capacity and general language abilities in people with aphasia was demonstrated. Unfortunately, the study of working memory in aphasia is fraught with methodological limitations, thus reducing validity and generalization of findings.

A. Nonlinguistic Deficits in Aphasia

There is increasing evidence that cognitive nonlinguistic deficits, such as deficits in attention, memory, speed of processing, and executive function ability accompany the more traditional linguistic deficits associated with aphasia. Performance of participants with aphasia on linguistic tasks was shown to be influenced by the manipulation of nonlinguistic factors, such as ambient noise level, rate of stimulus presentation, nonverbal alerting signals, and repetition of material.

Participants with aphasia were found to perform worse than language-normal controls in situations requiring them to alternate between two tasks and in situations requiring them to focus on certain items in the face of ongoing interference. Concomitant nonlinguistic tasks (e.g., tone discrimination) were shown to negatively impact receptive and expressive language abilities of individuals with aphasia. The experimental findings to date suggest that greater attention demands lead to poorer performance on linguistic tasks. Further, deficits in sustaining, focusing, switching, and controlling attention probably contribute to language processing deficits in individuals with aphasia.

In addition to attention, verbal short-term memory (STM) was found to be impaired in aphasia. Luria (1976) proposed that an STM deficit is an essential characteristic of a certain aphasia type (acoustic-mnestic aphasia). Vallar and Baddeley (1987) demonstrated that a reduced short-term store in an individual with left hemisphere damage led to difficulties in understanding long sentences, especially when the type of sentence varied from trial to trial. Burgio and Basso demonstrated that individuals with left hemisphere damage were significantly more impaired on tasks of short and long term memory compared to controls. However, they did not find an effect of aphasia on memory deficits, except in a paired-associate learning task, in which individuals with aphasia showed performance decrements compared to individuals with left hemisphere damage but no aphasia. Martin and Saffran (1997, 1999) found a positive relationship between STM and learning abilities for word lists in participants with aphasia. Also, recent studies demonstrated limited working memory (WM) capacity in aphasia.

Deficits in executive function skills were observed as well. Purdy (2002) demonstrated that participants with aphasia completing neuropsychological tests designed to evaluate goal-directed planning and cognitive flexibility exhibited decreased speed and efficiency (number of moves or trials required to complete the task successfully) compared to individuals without brain injury; deficits in cognitive flexibility were identified as well. Individuals with aphasia were also shown to have difficulty monitoring their own performance and appropriately evaluating task demands.

In summary, there is convincing evidence that: (a) there are cognitive nonlinguistic deficits in aphasia and (b) these cognitive nonlinguistic deficits tend to exacerbate the language impairment of persons with aphasia. In other words, in addition to loss of linguistic rules and operations, adults with aphasia experience problems with accessing those representations because of their nonlinguistic deficits. These postulations have important implications for both assessment and treatment of individuals with aphasia, and for understanding the nature of aphasia.

Due to the prevalence of nonlinguistic deficits and their impact on language processing, evaluation and treatment of individuals with aphasia should not be restricted to the language domain. When estimating prognosis and selecting appropriate treatment, it is important to base evaluation of aphasia severity on both linguistic and cognitive nonlinguistic aspects. When assessing language abilities, clinicians ideally should perform a screening of attention, memory, and executive skills. Additionally, it is important that clinicians assess cognitive nonlinguistic processing simultaneously with language processing to investigate interactions between cognitive nonlinguistic and linguistic deficits. One of the main challenges in assessing cognitive nonlinguistic deficits in persons with aphasia is that most traditional assessment tools of cognitive nonlinguistic functions rely heavily on language. That is, they require that people with aphasia understand complex verbal instructions and respond verbally. Therefore, performance on these tasks might be confounded by individuals' receptive and expressive linguistic deficits and provide a distorted picture of their cognitive nonlinguistic strengths and weaknesses.

Patterns of cognitive nonlinguistic deficits have important implications for treatment. While preserved cognitive nonlinguistic resources can help individuals with aphasia regain impoverished linguistic representations, concomitant cognitive nonlinguistic deficits make progression through treatment more difficult and less efficient. An emerging body of research suggests that treatment of specific cognitive nonlinguistic deficits, such as attention, perceptual processing, and memory, could lead to improvement not only in these cognitive nonlinguistic domains, but also in language abilities. Helm-Estabrooks, Connor, and Albert (2000) showed that two persons with chronic aphasia, who had reached plateaus in traditional language treatment, were able to make observable gains in linguistic auditory comprehension following a brief intervention specifically targeting sustained, selective, and divided attention. D. R. Francis, Clark, and Humphrey (2003) suggested that repetition training of sentences affected WM in participants with aphasia by increasing processing efficiency. Sentence repetition training improved performance on a backward digit span (but not forward digit span) task, and sentence repetition. It also led to a small improvement on comprehension tasks. Ansaldo, Arguin, and Lecours (2004) demonstrated that attentional resources, in addition to linguistic resources, influenced improvement in lexical semantic processing in an individual with Wernicke's aphasia.

In summary, studies aiming to elucidate the nature of cognitive nonlinguistic deficits associated with aphasia are important, both for developing valid and reliable assessment instruments and for providing optimal treatment. Results of such investigations will aid clinicians and researchers in understanding the intricate constellations of symptoms in aphasia. Theories regarding the nature of aphasia should incorporate both linguistic and nonlinguistic variables.

B. Working Memory: A Helpful Construct in Studying Language and Cognitive Nonlinguistic Deficits in Persons with Aphasia Compared to STM (defined as a capacity for temporary storage of presented information), the concept of WM places a stronger emphasis on the notion of active manipulation of information instead of passive maintenance. Over the past 30 years WM capacity has been found to be related to higher cognitive tasks, including learning abilities, verbal reasoning skills, math skills, and language comprehension. From this perspective, WM may be again contrasted with STM in that performance on STM tasks has not been found to be as strongly related to other specific cognitive capacities.

Given the evidence of a relationship between WM and language comprehension in normal language processing and evidence of limited WM capacity in individuals with aphasia, WM plays an important role in understanding the nature of aphasia. WM is hypothesized to supply necessary resources for language processing. It has also been suggested that WM provides mental resources for executive abilities that play "an important mediating role in the complicated task of human communication especially when routine processing schemas are no longer viable due to primary speech and language processing disorders". Furthermore, WM is closely related to the construct of attention and speed of processing. Some researchers propose that it is the capacity to allocate controlled attention to various components of the task that determines WM capacity. Others state that speed of processing is an important determinant of WM capacity. Therefore, further understanding of how WM is limited in individuals with aphasia is essential for enhanced insight into patterns of cognitive nonlinguistic deficits in aphasia and their interaction with language functions.

Despite over a decade of research on the nature of WM in aphasia, understanding of the construct remains limited. Studies published to date may be roughly classified into four categories:

1. Studies in which broad conclusions regarding the role of WM in language processing in aphasia were based on significant differences between WM capacity of participants with and without aphasia.

2. Studies that exploited specific aspects of performance of participants with aphasia on WM and linguistic tasks as evidence for general theories of WM.

3. Studies in which the impact of limited WM capacity on comprehension abilities of persons with aphasia were explored indirectly, using either computational modeling or simulation experiments. In these simulation experiments, participants without cognitive nonlinguistic and linguistic impairments were induced experimentally to perform similarly to individuals with aphasia.

4. Studies that ascribed observed patterns of linguistic performance on discourse and sentence comprehension tasks to WM limitations, without directly measuring WM.

Among the investigations listed above, only one addressed the nature of WM deficits in aphasia. Wright and colleagues (2007) explored whether WM capacity is differentially limited according to the type of linguistic information being processed. However, due to numerous confounds in the measures of WM employed in the study (discussed in detail in chapter II) and small sample size (only nine participants with aphasia and no control group), limited inferences can be drawn from the results.

To improve understanding of WM in aphasia, it is important to delineate whether WM limitations in aphasia are domain-specific or domain-general. If limitations in capacity are restricted to verbal WM, then it is essential to explore whether the limitations are specific to certain types of linguistic information. Additionally, the relationship between WM and linguistic processing in aphasia needs to be investigated in greater detail across a broad array of tasks. This will provide further insights into the role of WM in language abilities in individuals with aphasia. An investigation of submechanisms/constraints (such as phonological STM, attentional resource capacity and its allocation, and speed of processing) underlying limited WM capacity in individuals with aphasia and the contribution of these different mechanisms to various language abilities will enhance the conceptualization of aphasia. Studies of factors constraining WM in aphasia will have important implications for general theories of WM and for improved understanding of the nature of aphasia. Obtained information will also be relevant for designing clinical assessment tools and tailoring treatment to the individual needs of persons with aphasia.

Despite recent advances in WM research and increased interest in WM deficits in aphasia, tasks used to measure WM in individuals with neurogenic language disorders have substantial methodological limitations. Consequently, many of the studies reported have confounds that limit the inferences that may be drawn regarding the role of WM in language processing in aphasia. Methodologically sound measures appropriate for persons with aphasia must be established to investigate WM in aphasia in greater detail and with improved empirical validity.

Given that it is important to understand the theoretical reasoning underlying the development and structure of WM tasks, a brief review of theories of WM is presented, followed by description of WM tasks and measures.

C. Baddeley's Multi-Component Theory of Working Memory

In 1974, Baddeley and Hitch proposed that a passive STM system assists an active WM system. Since that time, numerous theories have been proposed to explain the structure, functions, and mechanisms of WM. Nevertheless, the original theory of WM promoted by Baddeley and colleagues, along with its later modifications, has remained highly influential. At first, Baddeley and colleagues (1974, 1999) described a triadic structural model of WM. The control system within this model, termed the central executive, represents a pool of limited attentional resources and is responsible for allocating processing capacity to its various components and processing of information within WM. The central executive was initially said to be subserved by two "slave" systems: the phonological loop and visuo-spatial sketchpad (the visuo-spatial sketchpad was later divided into spatial and visual subsystems). These two systems are used for short-term storage of modality-specific information. The phonological loop is said to play an important role in language processing because it is responsible for maintaining verbal information in short-term storage via mechanisms of rehearsal. Later, Baddeley (2000) added another "slave" system to the model: the episodic buffer, which is said to be capable of storing multimodal information and integrating it to form holistic episodic representations.

D. Just and Carpenter's Single-Resource Theory of Working Memory

Just and Carpenter (1992) proposed a different model of verbal WM. According to their view, WM represents a unitary capacity (rather than a set of distinctive subsystems) that is available for both storage of incoming input and intermediate products of computation and concurrent processing of this input. Whenever demands of a task exceed the total activation available, a trade-off between storage and processing occurs, and either one or both are compromised. Individual differences in WM capacity lead to both quantitative and qualitative differences in speed and accuracy of language comprehension. While Just and Carpenter limited their discussion to WM associated with processing of verbal material, their colleagues Shah and Miyake (1996) separated WM dedicated to language from WM capacity for spatial processing, thereby suggesting the idea of domain-specific WM resources.

E. Caplan and Water's Theory of Working Memory Specialized for Syntactic Processing Arguing against the unitary nature of WM for language processing, Caplan and Waters (1996, 1999, 2004) stated that a distinct and independent module within the general verbal WM, called the "separate sentence interpretation resource", was responsible for syntactic processing. According to their account, damage to this module leads to depletion of processing resources necessary for on-line syntactic analysis, thereby causing syntactic comprehension deficits in people with aphasia.

F. Attention Approaches to Working Memory

Not all researchers subscribe to the notion of a domain-specific WM. An attentional approach to WM that regards WM as a domain-free capability has become prevalent in the cognitive psychology literature within the last 10 to 15 years. While there are subtle distinctions among the views promoted by different researchers, a common theme is that WM capacity is not dependent on the domain of processing, but rather is determined by the general ability to allocate attention between two components of a given task, keeping relevant information activated despite possible ongoing interference. Engle, Kane, et al. (1999) likened WM capacity to the capacity of controlled attention, stating that "working memory capacity reflects the ability to apply activation to memory representations, to either bring them into focus or maintain them in focus, particularly in the face of interference or distraction".

A prominent and distinct account of WM within the attentional approach is Cowan's embedded processes model (1995, 1999). In his view, WM memory is a hierarchically organized system that is part of long-term memory (LTM). All processing mechanisms involved in maintaining information in an accessible state are considered to be part of WM; these include activated memory and focus of attention. Traces of LTM that are activated beyond a certain threshold make up activated memory or STM. Items in STM that are being processed at a given moment are described as being in the focus of attention (also referred to as span of apprehension). STM is temporally limited. That is, items that are not rehearsed or processed further decay within a certain time period. To keep items from fading away, attention intermittently must be allocated to them. In other words, they must periodically enter the focus of attention. Focus of attention is capacity limited; it depends on how many distinct items an individual can attend to at a given point in time without relying on rehearsal or cognitive/mnemonic strategies. The span of apprehension has been shown to steadily increase from childhood to adulthood and to be related to scores on aptitude tests. According to Cowan (1999) adults on average can focus on four things at a time. Individual differences in span of apprehension lead to differences in cognitive abilities. The more things a person can attend to simultaneously the more apt he or she is to perform well on higher-level cognitive tasks.

G. Other Approaches to Working Memory

Alternative explanations regarding mechanisms limiting WM capacity have also been proposed. Hasher and Zacks (1993) suggested that reduced capacity for verbal processing is due to an inability or limited ability to inhibit irrelevant information, rather than limitations in WM activation itself, as originally advocated by Just and Carpenter (1992). MacDonald and Christiansen (2002) highlighted the role of prior linguistic experience in determining both WM capacity and language comprehension. They equated the notion of capacity with that of processing efficiency which is "a function of the input (e.g., whether the material is complex or simple), the properties of the network (how activation is passed through weights, etc), and the interaction of these properties—how much the network has experienced similar input before". Consequently, MacDonald and Christiansen do not regard WM as a distinct entity within cognition because it "cannot vary independently of the architecture and experience that governs the network's processing efficiency". Instead, MacDonald and Christiansen considered capacity to be a trait of the network itself in which long-term language knowledge and computational capacity are inseparable. Therefore, according to their view, WM and language tasks provide different means of indexing language processing, and there is no need to recruit an additional construct, such as WM, to explain experimental results obtained by Just and Carpenter, or Caplan and Waters (1999, 1996).

Towse, Hitch, and Hutton (1999, 2000) criticized Just and Carpenter's theory (1992) from a different perspective. They stated that there is no trade-off between storage and processing and advocate for a task-switching rather than a resource-sharing strategy in completion of WM tasks. According to Towse and colleagues (1999, 2000), individuals switch their attention and resources between different tasks (i.e., processing and storage), rather than distribute them simultaneously. They proposed several alternative mechanisms that might lead to individual differences in WM span. These mechanisms include the duration of the retention interval, the rate at which representations in memory degrade, and processing speed. Participants who engage in processing for longer durations will have to retain representation in memory for longer periods, which, in turn, will lead to greater time-based forgetting or decay. Case (1985), in particular, attributed developmental increases in WM capacity to increased speed of mental operations as these operations become more automatic. This view is supported by an extensive literature on speed of processing, in which speed of mental operations is regarded as the basic underlying mechanism of individual differences in cognition within and across age groups.

In summary, theories of WM are equivocal with respect to the nature of WM and the mechanisms that may limit its capacity. Perhaps varying explanations will be shown to be complementary as work in this area continues. To understand more comprehensively the construct of WM, researchers must account for disparate findings to date and further develop experimental methods suitable for use with various populations, including children, elderly adults, and individuals with nonlinguistic and linguistic cognitive impairments.

H. Working Memory Tasks

Just as the concept of WM evolved from the notion of STM, WM measures have evolved from measures of STM. Traditional STM tasks (simple span tasks) entail presentation of items followed by their immediate recall. In these tasks, presentation of items starts with short list lengths (usually two) and proceeds to longer lists until participants can no longer accurately recall the items in the correct serial order. The participant's STM span is determined by the longest list length recalled perfectly.

Given that WM has been defined as the capacity to engage simultaneously in processing and storage, the tasks used to evaluate WM capacity must engage both of these functions. Therefore, unlike traditional assessments of STM, which entail only storage (and consequently mental rehearsal of items to be recalled), WM measures require a dual-task condition. These dual-task conditions involve both a storage and a processing component: the processing task is thought to interfere with the storage task demands. However, it is erroneous to assume that any task requiring concurrent storage and processing of information can be used to index WM capacity. WM tasks must be carefully designed and the psychometric properties of associated performance measures must be established prior to making inferences regarding WM limitations in different populations.

I. Working Memory Complex Span Tasks

WM span tasks (often referred to as complex span tasks) are among the most widely used measures of WM. In a typical complex span task, a processing task (e.g., sentence reading, arithmetic problem-solving, visual-spatial tracking), is given along with a set of stimuli (e.g., letters, words, shapes) to be remembered for later recall. There are two primary types of complex span tasks: verbal and nonverbal (or visual-spatial). Among the verbal span tasks, reading and listening span tasks were the first to be developed. The notion of a unified capacity for storage and processing served as the theoretical foundation in the design of these tasks. This theory later evolved in what is known today as the Just and Carpenter's (1992) single-resource theory of WM.

In the initial reading span task participants were required to read aloud sentences that were presented in sets of 2 to 6 sentences (processing component), and at the same time remember the last word of each sentence (storage component); three sets of each size were presented. At the end of each sentence set, participants were asked to recall the sentence-final words in the order in which they were presented. This task, compared to traditional measures of STM, was assumed to have greater processing demands, which would lead to a noticeable trade-off between processing and storage; this, in turn, would be more like a situation commonly encountered in language comprehension. More efficient readers would have more resources to devote to storage of to-be-remembered items, demonstrating a larger WM span. Following the authors' predictions, the results of the first experiment showed that performance of college students on the reading span task correlated strongly with performance on reading comprehension tests (verbal SAT and experimental narrative comprehension tasks), while STM span was not significantly related to comprehension abilities. In the second experiment, Daneman and Carpenter modified the processing component of the task, to ensure that participants were not solely concentrating on the final words as they read aloud, but that they were actually paying attention to the meaning of the sentences. They required participants to validate the truth value of each sentence after reading it. Additionally, they tested the relationship between reading and listening span tasks. The listening span task was different from the reading span task in that sentences were presented auditory. As was hypothesized, Daneman and Carpenter found that performance on the two span tasks was highly correlated. All three WM span measures (silent and oral reading span tasks and the listening span task) were significantly related to performance on general auditory and reading comprehension tasks. According to Daneman and Carpenter, the background processing task plays a leading role in determining WM span because those individuals who are more efficient in this type of processing (in this instance, reading or auditory comprehension) have more capacity to devote to remembering the words to be recalled. According to their theoretical framework, it is the efficient reading/auditory comprehension that leads to a larger WM capacity as indexed by complex reading/listening span tasks. WM capacity is regarded as being specific to the domain of the processing task. Therefore, if the span measure is to predict individual variations in reading comprehension it must include a processing task that requires reading or language processing (e.g., auditory comprehension).

Since Daneman and Carpenter's (1980) seminal study, different aspects of the reading/listening span task have been modified. Also, additional span tasks have been developed to assess verbal working memory. These include operation and span tasks. The general structure of these tasks is similar to the reading span task. Development of these verbal span tasks was partly motivated by the notion of a general WM capacity, rather than a WM capacity dedicated exclusively to linguistic processing. Consequently, studies employing different verbal span tasks provide evidence that factors beyond prior language experience impact performance on WM tasks. Turner and Engle (1989) hypothesized that WM capacity is independent of the type of processing in which an individual is engaged, as it represents a pool of general processing resources. This is a concept that is fundamental to an attentional approach to WM, in contrast to Daneman and Carpenter's (1980) view of domain specific processing.

In Turner and Engle's operation span task, participants (college students) saw, heard, and read simple arithmetic equations and were required to verify a given answer, while remembering words presented after each equation. As in the reading/listening span tasks the number of operation strings in a trial (i.e., set size) increased from 2 to 5. Turner and Engle demonstrated that results of the operation span task were strongly correlated with reading comprehension ability and verbal SAT scores. The relationship remained significant even when quantitative SAT scores were included as covariates. This eliminated an alternative explanation that the relationship between operation span and reading comprehension is due to a general tendency of reading and math abilities to be significantly related. The authors suggested that individuals with larger WM capacity are better able to perform various cognitive tasks because they can focus on, attend to, and remember more things at once. These abilities lead to both a larger WM span and higher scores on tests of higher-level cognitive abilities. This is different from the explanation offered by Daneman and Carpenter, who suggested that efficient language skills are the reason for better performance on reading/listening complex span tasks.

To further study the impact of the processing task on WM capacity, Turner and Engle (1989) manipulated the difficulty of the processing task embedded in a complex span task. Higher correlations between performance on complex reading and operation span tasks and reading comprehension were observed when the processing task was moderately difficult, but not too easy or too hard for the participants. This further supports the notion that the relationship between complex span and language comprehension is largely independent of the nature of the background task. Also, this observation has important methodological implications for the design of complex span tasks in general. On one hand, if the processing component is too easy, then the span task starts to resemble a simple span task, which diminishes its predictive power. On the other hand, if the embedded task is too difficult, then it may lead participants to allocate most of their processing capacity to it, resulting in a restricted range of span scores.

The counting span, sometimes also called dot working memory span, was developed by Case and colleagues (1982). In this task, participants (elementary school children and adults) were instructed to search for green dots amongst yellow dots on a screen and then remember the total number of target dots for later recall. Although seemingly different from the reading and operation span tasks, the counting span task incorporated both storage and processing components, and results obtained on this task correlated with measures of general intelligence. In a study where all three verbal complex span tasks were presented to 133 college students with a wide range of scholarly ability levels (verbal SAT scores ranging from 300 to 800), significant moderate correlations were obtained between the measures of WM. Also, a significant relationship was observed between measures of fluid intelligence and WM. A later study found even stronger positive correlations among different verbal WM span tasks (from 0.55 to 0.79) completed by 236 adults between 18 and 35 years old without any neurological impairments who had diverse academic abilities, suggesting that they all tap the same construct. It was later proposed by Conway and colleagues (2005) that counting span because of its nonlinguistic and relatively simple arithmetic processing component, is suitable for use with elderly individuals, speakers of different languages, and participants with language and cognitive nonlinguistic impairments.

Another type of complex span task is nonverbal or visualspatial. The processing component of these tasks incorporates a spatial task (e.g., rotating letters, deciding on the symmetry of a design, mentally tracing a letter) along with a storage task of memorizing spatial information for later recall (e.g., size of arrows, position of cubes in a matrix, direction of a ball's movement). Kane and colleagues (2004) demonstrated that performance on spatial WM tasks was correlated with performance on traditional verbal span tasks, such as reading, operation, and counting span (correlations ranged from 0.49 to 0.60). Results of confirmatory factor analysis also supported the conclusion that working memory capacity was not specific to the domain of the processing task; a one-factor WM model best accounted for the performance on the visuospatial and verbal span tasks (Kane et al., 2004). However, Shah and Miayke (1996) obtained results contrary to these findings. In their study performance of 54 college students on a spatial working memory task was not significantly related ($r(52)=0.2$, $p>0.10$) to performance on a reading span task. It is possible that the complex spatial span task in this study was more a measure of short term storage than WM capacity, as a high correlation ($r(52)=0.52$, $p<0.01$) was observed between complex spatial span and simple arrow span performance.

Psychometric data are available for verbal (reading, operation, counting) and spatial complex span tasks. These psychometric properties were established on large samples (with at least 50 and often more than 100 participants in each study) and, therefore, can be interpreted to be stable characteristics of these tasks. Verbal WM span tasks were repeatedly shown to have high internal consistency as measured by split-half reliability. Alpha coefficients were above 0.7 in each of these studies for all verbal span tasks; except the reading span task in Engle, Tuholski et al. study (alpha was 0.53). An alpha coefficient of 0.7 and above is a widely accepted criterion signifying that a measure has sufficient reliability. Spatial WM span tasks were not investigated as widely and internal consistency for these tasks was reported in only one study (ranging from 0.47 to 0.61). Also, performance on verbal WM span tasks was shown to be relatively constant over time (from minutes to more than several months) with test-retest reliability being in the range of 0.7-0.8 for reading and operation span, though some studies reported values from 0.41 to 0.65. A significant shortcoming of the psychometric properties of the complex span task performance reported to date in the literature is that they have been established exclusively using data from young adults (mostly college students) who do not have neurological or language impairments.

Performance on WM span tasks was consistently related to performance on a broad array of higher-order tasks, such as verbal reasoning, listening and reading comprehension, following directions, math skills, and learning ability. WM span measures were also shown to correspond to performance on low-level attention tasks, such as the antisaccade probe. Successful performance on this task requires controlled attention because the goal of the task needs to be maintained in the face of interference via suppression of reflexive eye movements. Kane and colleagues (2001) developed an antisaccade probe in which a flashing cue appeared to the right or left of the fixation point; 50 milliseconds after that the target letter was presented on the opposite side of the screen.

The participants (college students with normal or corrected to normal vision) had to identify the target letter as quickly as possible by suppressing a reflexive saccade towards the flashing cue and in turn directing their gaze in the opposite direction. Reaction time and accuracy of fixation and letter identification were used to index performance. Participants with high WM span performed the task faster and more accurately than participants with low WM span. The observed relationship between WM capacity and controlled attention suggests that complex span tasks tap into domain-general capacity for controlled processing.

J. Other Working Memory Tasks

Sometimes tasks other than complex span tasks are used to investigate WM capacity. These tasks can be roughly grouped into four categories depending on their structure.

First, processing may be carried out on the same items that are to be stored. For example, in the backward span task participants are instructed to recall a list of spoken items in the reverse order. In a letter number sequencing task, letters and numbers are presented together with one another, with participants first repeating numbers, then letters in sequential order.

Second, instead of alternating the processing and the storage components as is done in complex span tasks, an entire set of items to be stored is presented first, followed by a processing task, and then recall. This sequence is repeated several times. Because proactive interference is said to accumulate, each trial supposedly requires greater WM resources for successful recall than the previous trial. Such tasks are referred to as Brown-Peterson-type tasks. For example, in one study employing this form of task, participants were (a) presented with a list of words, (b) asked to complete an oral version of the Trail-Making Test, and (c) instructed to recall the words. Several word lists were tested in this manner.

Third, tasks of immediate dynamic memory require participants to monitor continuously a string of stimuli and respond only to a specific subset. Examples are running span, keeping track, and N-back tasks. In running span tasks, stimuli in lists of varying length are presented, and participants are required to recall the last n items from the list. Similarly, in keeping-track tasks, lists of items of unknown length are presented and participants have to retain only the last item from each category. In N-back tasks, participants are instructed to judge whether an item matches a previous one presented n items before.

Finally, a different WM task was proposed by Cowan (1999). According to his embedded processes model of WM, the focus of attention plays a critical role in cognitive processing. Therefore, WM tasks should aim to index this capacity specifically. Traditional span tasks, such as reading or operation span, yield estimates of the focus of attention because the concurrent processing task prevents participants from rehearsing the items to be recalled. However, according to Cowan, complex span tasks have many confounds associated with them (e.g., speed-accuracy trade-offs and use of different strategies across participants, such as attention sharing or switching). For this reason WM researchers should use more basic and precise measures. Cowan et al., (2005) advocate the use of the unattended speech task or memory for ignored speech task to index the focus of attention. In this task, verbal lists are presented auditory to the participants along with a computerized picture matching task. Periodically, a recall probe comes up on the computer screen and participants have to recall the last words presented to them in the order that they were presented. The picture matching task is supposed to prevent participants from chunking, rehearsing, or using other cognitive strategies to remember the words.

Much less evidence pertaining to the internal consistency, reliability, and validity of these various WM tasks is available. One of the main concerns with these tasks is that it is impossible to appraise the difficulty of their corresponding processing components. In turn, it is difficult to evaluate whether and how distinct they are from simple span tasks indexing STM. In addition, factors, such as rate of stimuli presentation for the running memory task, number of categories used in the keeping-track task, duration and number of items back in the N-back task, have not been explored in sufficient detail to understand how they might impact performance. Due to these complications, mixed results are often obtained regarding the correspondence between performance on these tasks and on traditional WM tasks. Therefore, using these measures without providing clear evidence of their conceptual and psychometric soundness may lead to erroneous conclusions. For example, N-back tasks have been widely used in neuroscience research as a measure of WM. However, the few studies that investigated their validity have yielded inconclusive results. R. Roberts and Gibson (2002) found a zero correlation between performance of young participants without cognitive nonlinguistic or linguistic impairments (n=30) on N-back and complex span tasks; performance on both of these tasks was significantly related to measures of sentence comprehension. Kwong See and Rayn (1995) reported that N-back and simple span tasks accounted for similar variance in language comprehension. In a recent study, Kane et al. (2007) investigated behavioral construct validity of N-back tasks on individuals without cognitive nonlinguistic or linguistic impairments (n=132). They demonstrated a weak association between performance on 2- and 3-back tasks and operation span task; correlations ranged from −0.08 to 0.22, and only two out of eight were significant at the 0.05 level. Also, the two types of WM tasks accounted for independent unique variance in fluid intelligence. These results demonstrated that although N-back tasks seem similar to traditional complex span measures and may also index abilities related to cognitive processing, the evidence to date does not warrant their direct association with the construct of WM.

Equivocal results have also been obtained with backward span tasks. Studies of adults without any neurological impairments have shown both that performance on the backward span task loads on the same factor as complex span tasks, with contrary results reported by Engle, Tuholski, et al., (1999). Therefore, it is advisable to ensure convergent validity of results obtained on novel or infrequently used measures of WM with more established indices, such as well-studied complex span tasks.

K. Scoring of Working Memory Tasks

In addition to variability associated with the structure of WM tasks, there are methodological complexities related to scoring of performance on WM tasks. Schemes for evaluating performance on WM tasks and determining a person's WM capacity have become almost as diverse as the tasks themselves. In this section, the critical principles for evaluating performance on WM tasks will be addressed and the main scoring procedures will be described. Although the discussion below is based on the literature about complex span tasks, the issues raised are applicable to most WM measures.

One of the main questions that arises with scoring performance on all dual-task conditions is how to incorporate performance on two components of the task (in the case of WM tasks, processing and storage) into a single score. Studies of adults without cognitive impairments tend to ignore the processing component of the WM span tasks. In the initial WM span task used by Daneman and Carpenter (1980), the processing component was not measured at all, as participants simply had to read the presented sentences. In later studies, even though specific comprehension questions or true/false judgments were employed in WM tasks, performance on these questions/judgments was not taken into account in computation of the final score. There are several reasons for this. First, the processing component of complex span tasks is usually relatively easy for individuals without any cognitive nonlinguistic or language impairments. Additionally, participants are instructed to focus both on the processing and storage components of the task, so that they do not overly prioritize the storage part while ignoring processing items. Not surprisingly, most individuals without cognitive nonlinguistic or language impairments perform at the ceiling level on the processing task. Given the prevalent ceiling effect, as a rule of thumb, data of participants whose accuracy falls below a certain cutoff (usually below 85%) are eliminated, while minor deviations in accuracy are still treated as "normal" performance (i.e., anyone scoring above 85% on the processing part is assumed to have "perfect" accuracy).

Second, the reason why performance on the processing component is not taken into account in the computation of the final score is that it has been empirically demonstrated that performance on the two separate components of the WM span tasks is positively correlated (despite a lack of variability in the processing component). This has been generally regarded as evidence of a lack of trade-off between processing and storage, leading most researchers to assume that an index of just one of the components is representative of overall performance. However, not all investigators share this viewpoint. Waters and Caplan (1996) obtained positive correlations ranging from 0.03 to 0.44 (about half of them significant) between errors on a processing component (sentence acceptability judgments) and recall errors in a series of complex reading span tasks. Despite the presence of a positive relationship, they argued that both components should be considered in estimation of WM capacity. To support this claim, they demonstrated that a composite Z score (derived by averaging final-word recall score alone, reaction time, and errors on the processing component within a task) from a complex span task only moderately correlated with the span score ($r=0.54$-$0.68$), as indexed by the final-word recall score. Further, correlations between general language comprehension measures and a composite Z score were higher ($r=0.49$-$0.72$) than between final-word recall score ($r=0.27$-$0.36$). According to the authors "these data suggest that much of the variance in the composite score measure is not shared by the reading span . . . measures". In other words, by eliminating the processing component from the final score (or not including it explicitly in the design of the task to begin with), considerable variance in performance is excluded from subsequent analyses. In summary, the tendency to disregard the processing component of WM span tasks is questionable even when participants are young adults without cognitive nonlinguistic or linguistic impairments and perform relatively well and stably on the processing component. When applied to special clinical populations such as individuals with neurogenic language disorders, disregarding the processing component could become even more problematic. This concern will be addressed in detail below.

In studies of individuals without cognitive, language, and neurological impairments the storage score is regarded as an index of WM capacity. The storage score does not simply reflect one's ability to recall items; rather it indicates individual's ability to remember and recall items during a processing task or in the face of ongoing interference. Thus, the storage score indexes overall WM capacity, whether it is defined as the ability to allocate attention between two tasks or as joint resource for simultaneous storage and processing. Several schemes exist for computing storage scores for complex span tasks.

Daneman and Carpenter (1980) used a quasi-absolute span score as an index of WM capacity. This score reflects the highest level (largest set size) that the participant can perform at a given threshold. For instance, if the participant correctly repeats words in at least three out of five sets of four sentences, but fails to recall words correctly for sets with five sentences, then he or she is assigned a span score of 4. Often performance near the threshold, such as recalling two out of five sets of a given size, is given partial credit (e.g., if the participant was able to recall correctly all words only for two sets of five sentences, his or her span score would be 4.5). However, this scoring approach was criticized for restricted variability in the range of values obtained, thereby weakening the ability to detect subtle differences among participants. As an alternative, item scoring was proposed to reflect the total number of items (instead of sets) recalled correctly. The two methods of scoring often provide similar results (correlations in the range of 0.8-0.9), and researchers tend to incorporate only one type of score in the analysis. Still, item scoring (particularly partial-credit unit scoring, where each set is scored as a proportion of correctly recalled items per set) is preferable because it provides greater statistical power and more closely approximates the normal distribution, compared to other scoring methods. Also, Waters and Caplan (2003) demonstrated that test-retest reliability is slightly higher for item compared to span scoring.

Span scores are often used to categorize participants into groups, such as high (top quartile) and low (bottom quartile) span groups. The two groups are then compared according to certain cognitive measures. Conclusions regarding the role of WM capacity in these tasks are based on observed differences (or lack of them). Such categorization has received the same criticism as span scores because it turns an interval-level variable into a categorical one, thus reducing statistical power. Furthermore, all participants within one group are treated as having the same span score, which is not valid. Additionally, classification into groups is not stable across time. Waters and Caplan (1996, 2003) repeatedly demonstrated that from 35% to 47% of individuals without neurological impairments (depending on the type of task) changed in terms of their classification from the first to the second administration of WM tasks.

One strategy to increase the reliability of WM scores across time and make the classification more stable is to use a composite WM measure derived from several WM tasks. Composite scores were shown to have higher test-retest reliability (0.85), compared to scores from single tasks (range from 0.61 to 0.78). According to Waters and Caplan (2003), classification of participants was also more stable when a composite score (based on alphabet, subtract 2, and sentence span tasks) was used for assigning participants into groups; only 16% changed their classification across two phases of the experiment. The reading/listening span task is influenced to some extent by verbal abilities, just as operation span is influenced by mathematical abilities. Given that no measure of WM is ideal and that each has associated confounds, it is important to use more than one measure of WM, so that conclusions may be drawn from a composite score.

An additional advantage of having several measures of working memory is that it is possible to conduct a latent variable analysis. This statistical procedure allows a latent variable (one that cannot be measured directly) to be derived from the common variance shared among several manifest variables. A number of studies using this method were conducted within the domain-general framework of WM. They defined WM capacity as the common variance between spatial, counting, operation, and reading spans. Latent variables of WM were shown to be more strongly related to fluid intelligence (as indexed by Raven's matrices) and this relationship was more consistent across different studies compared to individual complex span measures.

In summary, numerous tasks and measures have been designed to investigate WM capacity in individuals without cognitive nonlinguistic or linguistic impairments. It is important to recognize potential confounds inherent in measurement of WM capacity in individuals without any neurological impairments. These potential confounds include: the contribution of domain-specific abilities; a possible trade-off between storage and processing when only one component of the task is scored; the impact of the difficulty of the processing component on recall; and the accumulation of proactive interference across trials. Among a wide array of WM tasks, complex span tasks have evolved as the most common and widely accepted means of assessing WM, with the most psychometric data available. Various theories of WM regard performance on complex span tasks as valid indices of WM, even though different explanations have been offered as to why a span score represents WM capacity. Thus, complex span tasks have become a fairly standard means of measuring WM.

L. Study of Working Memory in Aphasia

Despite numerous broad references to the construct of WM and to the notion of limited capacity, few researchers have directly investigated WM and its relevance to aphasia. The discussion below will be focused on behavioral studies of WM capacity in individuals with aphasia.

Tompkins and colleagues (1994) initially demonstrated that participants with left hemisphere damage made more errors on a WM task than did a control group with no history of neurological impairment. Their findings were later expanded and substantiated by Caspari and colleagues (1998), who demonstrated an association between WM capacity and general language abilities in persons with aphasia. Friedmann and Gvion (2003) and Wright et al. (2003, 2007) further explored the relationship between working memory and linguistic comprehension.

M. Working Memory Complex Span Tasks

In most studies investigating WM capacity in individuals with aphasia, different versions of the original Daneman and Carpenter (1980) reading/listening span tasks with syntactically simpler and shorter sentences have been used. Starting with the first investigation of WM capacity in aphasia by Tompkins and colleagues (1994), sentences have been modified to ensure that the processing component is simple enough for participants with language impairment to achieve desired levels of accuracy because comprehension deficits are common among individuals with aphasia. Caspari and colleagues (1998) proposed another important alteration of the task by substituting recall of to-be-remembered items with recognition of pictorial representations of words; this minimized reliance on reading and expressive language abilities, which otherwise might have confounded results.

One of the first difficulties in analyzing research on WM in aphasia is that WM tasks within investigations have been modified in different ways, making the comparison or aggregation of data across studies problematic. In some studies, the content of the tasks and the procedures are not discussed in sufficient detail, making it difficult to interpret the results and compare findings with those of other studies. For instance, Friedmann and Gvion (2003) did not indicate whether the items in their span task were presented auditory, visually, or both. Additionally, the grammatical difficulty and length of sentences were not described. In Friedmann and Gvion' s study the listening span may have been unduly easy, given that individuals with aphasia performed less well on a STM task compared to a complex listening span task.

The content of the processing component is one of the most important facets to consider in development and later description of WM tasks. Both length and complexity have been altered simultaneously in tasks used to tap WM in aphasia. Potential effects of short but complex sentences or, alternatively, long but syntactically simple sentences have not been explored. Caplan, Waters, and Hildebrandt (1997) showed that syntactic complexity (canonicity of thematic roles in the sentence) and number of propositions (defined by Caplan et al. as the number of verb-related thematic roles) each had a separate impact on comprehension of sentences by individuals with aphasia. Later, Caplan and Waters (1999) emphasized that comprehension in persons with aphasia is especially vulnerable to increases in syntactic complexity because WM required for online sentence processing (the separate sentence interpretation resource) is impaired in individuals with aphasia. At the same time, researchers investigating STM in aphasia demonstrated that length of utterance, which directly impacts the number of items that must be activated to comprehend a sentence, is a critical factor underlying comprehension. It is possible that these two factors—length and complexity—have differential influences on performance of persons with and without aphasias on WM span tasks or that they will impact WM capacity of some individuals but not others.

Another important concern regarding the processing component of reading/listening span tasks is that often it entails true/false judgments. The required metalinguistic skills may pose additional problems for participants with language impairments. Comprehension questions entail fewer metalinguistic demands and may be considered to be more natural in terms of typical language use. However, presentation of a comprehension question following each sentence might involve excessive disruption for individuals with aphasia and may significantly interfere with their performance on the storage component of the task. To avoid this complication, Caspari et al. (1998) provided one or two randomly selected comprehension questions at the end of a set of sentences of the same length, to ensure that participants were attending to the content of the sentences. However, this is a problematic approach to measuring comprehension/processing of the presented materials because: (a) the processing task also involves storage, thus confounding the processing measure; and (b) the obtained data are insufficient for analysis of performance on the processing component of the task.

There is inconsistency across studies in terms of scoring methods; both span and item scores have been used. A partial-credit unit scoring system has been shown to yield greater statistical power compared to other scoring methods in participants without language or cognitive nonlinguistic impairments, but it has not been applied to data on persons with aphasia. Furthermore, in most studies comprehension of sentences is not assured. Only Wright et al. (2003) took into account both components of the task by incorporating accuracy of true/false judgments and recall into one score. The shortcoming of this method is that the same score may reflect completely different patterns of performance, thereby obscuring details about the nature of the relationship between WM and language abilities. Therefore, it is important to analyze measures of storage and processing separately. Additionally, Conway et al. (2005) and Waters and Caplan (2003) demonstrated advantages of using several measures of WM and deriving a composite score over any single WM measure in studies with participants who have no language or cognitive nonlinguistic impairments. Still, most studies of WM in aphasia have included solely one measure of WM. Friedmann and Gvion (2003), and Wright and colleagues (2007) used several WM tasks, but they did not report a composite score.

It cannot be assumed that the established high reliability and validity of traditional complex span tasks hold for adapted versions involving modification of content and structure. Limited attempts have been made to validate modified versions of WM span tasks. Caspari et al. (1998) conducted a preliminary evaluation of the substitution of the memory component from recall to recognition of pictorial representations of words on participants without neurological impairments. Caspari et al. found that a high correlation (0.57) between performance of 24 undergraduate students on a reading span task with a recognition component and reading comprehension (verbal SAT scores) was still present. The authors interpreted this result as evidence that changing the recall to a recognition task did not alter the construct validity of the WM task. However, directly concurrent validity of the modified task needs to be examined by correlating performance on complex span tasks with recall and with recognition. Also, participants in the Caspari et al. study were presented with long complex sentences, as in the original Daneman and Carpenter (1980) task. No published studies to date appear to have compared performance of participants without aphasia on the traditional complex span tasks and their simplified versions. There are no published psychometric data regarding modified versions of the complex span task.

Examining further the impact of simplified sentences on performance, the validity of comparisons between the aphasia and the control groups on these modified complex span tasks is not clear. Since the processing component is significantly simplified in these tasks, it is questionable as to how difficult such tasks are overall for adults without any cognitive nonlinguistic or language impairments and whether they reflect true WM capacity or simply short-term storage. Turner and Engle (1989) suggested that if the processing component of a WM span task is simplified then the task might become a simple STM task. This possibility cannot be excluded without further investigation. A related dilemma is that individuals with aphasia with mild receptive language deficits are likely to have a contingent advantage on these tasks, which would improve their WM scores regardless of their true WM capacity.

Apart from the lack of data on reliability and validity of the adapted reading/listening span tasks, there is another reason for cautiously interpreting the association between performance on WM and general language tasks in persons with language impairment. Modified span tasks and language items (i.e., standardized language tests and discourse/inference comprehension tasks) share common variance because they are both language based and require participants to process verbal stimuli in some way. The two measures may be correlated because they both assess the general severity of language impairment. However, Caspari et al. (1998) argued that the observed relationship among measures is not due to shared variance between the different tasks because these measures "are designed to assess different aspects of language, memory, and communicative functions and, therefore, differ in a number of ways". Caspari et al. further stated that the standardized language tests (Western Aphasia Battery [WAB] and Reading Comprehension Battery for Aphasia [RCBA]) used in their study measured different receptive and expressive language abilities, while WM tasks were not designed to assess linguistic abilities per se. Individual participant data from their study were analyzed by the first author of this manuscript. Listening and reading span scores were correlated with scores on the RCBA while controlling for severity of language impairment. The magnitude of the correlation decreased after controlling for severity; only the partial correlations between listening span (but not reading span) and the language test remained significant. Therefore, it is possible that the procedural and operational similarity between WM and language tasks leads to the significant relationship between them and that the severity of impairment is a common factor in both span performance and the level of language functioning.

Apart from concerns of concurrent validity and reliability of WM span tasks, it is critical to consider different processes that are required for successful completion of a complex WM task. Language impairment in aphasia is often accompanied by concomitant attention, hearing, visual, and motor deficits. Any such deficit unrelated to WM might interfere with performance on a complex span task. When constructing WM tasks and when analyzing performance of participants with aphasia, it is important to consider various stages of complex reading/listening tasks and their corresponding requirements, and account for possible alternative explanations.

N. Other Working Memory Tasks

N-back tasks have also been used to measure WM capacity in individuals with aphasia, e.g., in studies by Friedmann and Gvion (2003), and Wright et al. (2007). From a clinical perspective, they might seem more appropriate for individuals with aphasia, since the instructions for the task are straightforward and the task can be completed with a minimal verbal response. However, the use of N-back tasks to measure WM capacity has inherent problems of validity given that N-back tasks have been shown to have no significant correlations with performance on complex span tasks in adults without any cognitive nonlinguistic or language impairments.

Researchers have repeatedly indicated lack of agreement and scarcity of WM measures tailored for assessing persons with neurogenic language disorders. Several alternative tasks for indexing WM capacity have been recommended. The backward digit span from WMSIII has been proposed as a possible measure of WM for individuals with language impairment. However, a limited number of studies have used this measure with people who have aphasia. These studies are not described in detail above, as the investigators used the backward digit task from Wechsler in exactly the same format and they were not focused on investigating WM per se.

In one study the results achieved on a simple span (repeating numbers in the same order as they were presented) were treated as though obtained from a backward digit span; despite only addressing STM storage they were regarded as an indication of WM capacity. Connor and colleagues (2000)

suggested that both simple and backward digit span are measures of WM. This suggestion is problematic because STM tasks have repeatedly been shown to tap abilities different from those of WM tasks. Further, backward span tasks entail additional validity concerns as measures of WM memory because processing is performed on the same items that are to be stored; this greatly simplifies the task, possibly making it sensitive to something other than WM. This inherent confound may underlie the inconsistency in experimental findings between Engle, Tuholski, et al. (1999), who reported that backward digit span scores did not load onto the same factor as complex span scores, and Waters and Caplan (2003), who reported that they did. A letter-number sequencing task has been considered a more sound measure of WM from a theoretical standpoint; however, this measure would most likely be inappropriate for persons with aphasia because it entails complex verbal instructions. Also, construct validity of the letter-number sequencing task has not been widely established on individuals without cognitive nonlinguistic or language impairments.

There are many unresolved concerns regarding what WM tasks and measures are most valid and reliable for use with individuals with aphasia. It is evident that a measure developed on people without neurological impairment cannot be directly applied to individuals with aphasia because participants with aphasia tend to have numerous concomitant deficits. Consequently, their performance on WM tasks can be compromised by abilities unrelated to WM capacity. Also, the impact of the difficulty of the linguistic processing component on WM capacity of individuals with aphasia has not been thoroughly investigated. There is great need for research to establish methodologically, theoretically, and psychometrically sound measures appropriate for use with persons who have neurogenic language disorders. Development of such measures will enable more thorough and valid investigation of the role of WM in aphasia.

O. Additional Methodological Limitations

Apart from limitations related to the use of specific tasks and measures of WM, existing studies of WM in aphasia have other shortcomings common to research on aphasia in general. Unfortunately, most authors present limited information about participants with aphasia. In some studies participants with aphasia were not screened for hearing or visual acuity, even though intact visual and hearing perception are required for completion of WM tasks. In one study, data from participants with aphasia were not analyzed separately from individuals with left hemisphere damage but without language impairment. Similarly, in a different investigation five participants from the aphasia group had an aphasia quotient on the WAB above the cut-off for normal performance (93.8) and high RCBA scores (ranging from 92 to 99); however, their data were combined with data from other participants, without providing further evidence of any language impairment. Therefore, it is not clear how aphasia was diagnosed. An additional problem is that it is difficult to generalize findings from other studies due to a small number of participants with aphasia. A related limitation is that parametric statistics are often inappropriately applied to data collected from a small sample. Nonparametric statistics are more appropriate in such cases due to less strict assumptions about the distribution of the population from which the data have been sampled.

P. Control for Confounding Factors

Complications associated with current WM tasks and measures and their applications for individuals with aphasia have been outlined. WM span tasks are regarded as a standard means of assessing WM capacity in adults without cognitive nonlinguistic or language impairments. For this reason, they have been the focus of further modification in the development of tasks for individuals with aphasia. Other WM tasks may not be invalid, but less evidence substantiating their reliability and validity is available. Use of WM tasks with established reliability and validity will enable legitimate comparisons of WM capacity between individuals with and without aphasia. Further, complex span tasks and associated WM measures are consistent with the theoretical conceptualization of WM as a capacity for storage of information during processing or in the face of ongoing interference, with contributions from both domain specific and domain-general mechanisms. Our work in this area is not intended to provide support for any specific theory of WM or delineate a theory that would best explain WM deficits in individuals with aphasia. Establishing validity and reliability of tasks and measures of WM for individuals with aphasia will support future investigations aiming to test competing theories of WM.

Apart from areas of control listed above, it is vital to provide assurance of reliability and validity for any new or modified tasks and measures in studies of people with and without aphasia. It is important to ensure that modified tasks have high concurrent validity in relation to traditional WM tasks in people without cognitive nonlinguistic or language impairments. Eventually, procedures and scoring methods must be standardized to enable comparisons across studies and conduction of metaanalyses. Overall it is best to use several measures of WM in parallel so that a composite score can be computed and/or latent variable analysis performed.

Additionally, it is important that research on WM in aphasia adhere to general guidelines for aphasia research. It is crucial to provide a detailed description of participants, which should minimally include demographic characteristics, results of vision and hearing screenings, neuroimaging data, description of language impairment, a rationale for aphasia diagnosis, and indications of any concomitant cognitive nonlinguistic, psychiatric, and motor deficits. Appropriate statistical methods should be used.

Empirical evidence accumulated over years of experimental inquiries across many disciplines has designated WM as an important construct for elucidating individual differences in various domains of cognitive functioning. Contribution of WM to various linguistic skills has been demonstrated in numerous studies. The role of WM in language processing in aphasia has been subjected to preliminary investigations. However, in order to fully exploit the construct of WM for elucidation of linguistic and cognitive nonlinguistic deficits in neurogenic language disorders, measures that have sound theoretical, methodological, and psychometric properties must be developed.

In view of the foregoing, it would be advantageous to provide cognitive and linguistic assessment methods that incorporate an alternative response mode that requires no talking, writing, gesturing, or instrument manipulation for accurately assessing patients who have difficulties in these response modalities. It would further be advantageous to provide such methods that permit stimulus adaptations to control for perceptual, attentional, and oculomotor deficits. It would further be advantageous to provide such methods that minimize reliance on participants' understanding of instructions prior to the presentation of testing stimuli. It would further be advantageous to provide such methods that permit a continuous record of processing, simultaneous with the assessment task, without interruption of the task with intervening verbal instructions, prompts for responses, or demands for patients' conscious planning of responses.

BRIEF SUMMARY OF THE INVENTION

In accordance with the objectives of the present invention, there are provided several methods for assessing linguistic and cognitive processing in patients through the use of eye tracking measures. These methods allow us to gain information about intact comprehension and cognitive ability that is currently unavailable for many severely inexpressive patients. Assessment through eyetracking minimizes confounds associated with traditional means of cognitive and linguistic assessment, even in people without neurological disorders.

The use of eye tracking in language comprehension tasks requires that the inventive methods include strategies to ensure that the "eye-mind hypothesis," also referred to as the "eye-mind assumption," is valid. It is the essence of this assumption that the "eye fixates the referent of the symbol currently being processed if the referent is in view". That is, viewers tend to look at objects or images that they are thinking about. Accordingly, a patient being assessed does not need to understand any instructions and is not required to consciously manipulate any devices, such as a computer mouse, a joystick, or a button. Assessment through eyetracking allows: stimulus adaptations that may serve to control for perceptual, attentional, and ocular motor deficits in the differential diagnosis of language processing difficulties; reduced reliance on patients' understanding and memory of verbal instructions prior to testing; allowance for a real-time measure of comprehension; and allowance for testing of a broad range of verbal and nonverbal stimulus types. Moreover, eye movements are often preserved even in patients with severe motoric and cognitive deficits.

A first of the inventive methods is directed toward the assessment of linguistic comprehension using eyetracking. In accordance with the method, a patient is first seated in front of a computer monitor. A conventional remote pupil-centered corneal reflection eyetracking system is then configured to track the patient's eye movements. Next, a clinician simultaneously provides the patient with a pre-recorded verbal stimulus and presents the patient with an associated visual stimulus on the screen of the computer monitor. The visual stimulus includes four separate images positioned in the four corners of the screen. One of the images is a "target" image that corresponds to the verbal stimulus, and the other images on the screen are "non-target" foils that do not correspond to the verbal stimulus. The patient is preferably instructed to "look at the images on the computer screen in whatever way comes naturally."

As the patient views the display in a natural manner the eyetracking system, in cooperation with customized computer software, measures and records fixation location data (i.e., data representing where the patient looks) and fixation duration data (i.e., data representing how long the patient fixates on particular areas of the display). The proportion of the duration of the patient's total visual fixation time that is allocated to the target image has been found to be a reliable indicator of whether or not he or she understood the verbal stimulus, and therefore provides an accurate measure of the patient's level of linguistic comprehension.

A second of the inventive methods is directed toward assessing the effect of semantic associative priming on a patient. In accordance with the method, a patient is seated in front of a computer monitor and an eyetracking system is configured to track the patient's eye movements as described above. Next, the patient is told that he or she will see words and picture sets on a computer screen. The patient is told to read the words and to look at the pictures on the screen in a natural manner.

Next, the patient is presented with successive arrays of picture stimuli and corresponding high-association prime words on the screen. Each prime word is presented textually in the center of the screen and the picture stimuli appear in three corners of the screen. One picture in each set represents a high semantic association with the prime word, whereas the other two pictures represent a low association with the prime word.

As the picture stimuli are presented, custom software allows analysis of the patient's raw eye-fixation measures. Fixation duration measures provide a reliable indicator of the effect of semantic associative priming on the patient. For example, a greater proportional duration of the patient's fixations on pictures having high semantic associations with prime words correlates with a greater effect of semantic associative priming on that patient.

A third of the inventive methods is directed toward the assessment of working memory. In accordance with the method, a patient is seated in front of a computer monitor and an eyetracking system is configured to track the patient's eye movements as described above. Next, the patient is provided with the following instructions: "you will see pictures and hear sentences. Listen to the sentences and look at the pictures. Remember the colors or shapes that you see. Then look at the corner with the colors or shapes you just saw."

Next, the patient is presented with a multiple-choice picture array displayed on the computer monitor accompanied by a prerecorded verbal stimulus that corresponds to one of the images in the array. Following the multiple-choice array a color box or symbol to be remembered (a "storage item") is presented in a separate display. Several multiple-choice arrays, each one followed by the presentation of a storage item (color or symbol), are presented in series. At the end of each sequence a "recognition screen" containing various combinations of symbols or colors in each quadrant of the display is presented to the patient. One of the combinations (the target) corresponds to the combination of all of the symbols/colors presented to the patient in the preceding series.

As the picture stimuli are presented, the eyetracking system and custom software allow analysis of the patient's raw eye-fixation measures. Previous research on participants with and without language impairment has shown that the proportion of fixation duration on the target image within an array is a valid and a reliable measure of comprehension ability.

A fourth of the inventive methods is directed toward the assessment of attention allocation. In accordance with the method, a patient is seated in front of a computer monitor and an eyetracking system is configured to track the patient's eye movements as described above. Next, a single-task condition visual search task is administered wherein the patient is presented with a series of multiple-choice image displays on the computer monitor. Each display contains one target image and three foil images. All of the images share a variety of image characteristics. The three foil images are identical while the target image differs with respect to a single image characteristic (e.g., orientation). After three seconds an examiner instructs the patient to "look at the different image"

Next, a single-task condition comprehension task is administered wherein the patient is first instructed to "listen carefully to the words." A verbal stimulus is then presented to the patient while the patient looks at a blank computer screen. A multiple-choice image display is then presented to the patient wherein four images are displayed in the four corners of the screen. One of the images is a target image that corresponds to the verbal stimulus and the other three images are nontarget foils.

Next, a series of dual-task trials is administered to the patient. Accordingly, the patient is instructed to "look at the different image and listen carefully to the words." Next, while tracking the patient's eye movements, the patient is simultaneously presented with the visual search task (described above) and a verbal stimulus. A multiple-choice display containing one target image corresponding to the verbal stimulus and three nontarget foils is then presented to the patient.

A patient's eye-fixation duration measures steps have been found to be a reliable indicator of a patient's ability to allocate attention resources. Specifically, a greater decrease in the duration of such measures when comparing a patient's performance in the dual-task condition to his or her performance in the single-task condition correlates with a greater deficiency in the patient's attention allocation.

With regard to all of the methods described above, clinical research has demonstrated that our methods are significantly more accurate at assessing the level of impairment in patients with brain injury, for whom it is often difficult to assess comprehension.

BRIEF DESCRIPTION OF THE SEVERAL VIEWS OF THE DRAWINGS

FIG. 7 is an illustration of a sample prime word and an associated visual stimulus used in the method for testing semantic associative priming of the present invention.

FIG. 12 is a table of characteristics of simple and complex sentences used in the method for testing attention allocation of the present invention.

Figure 1:
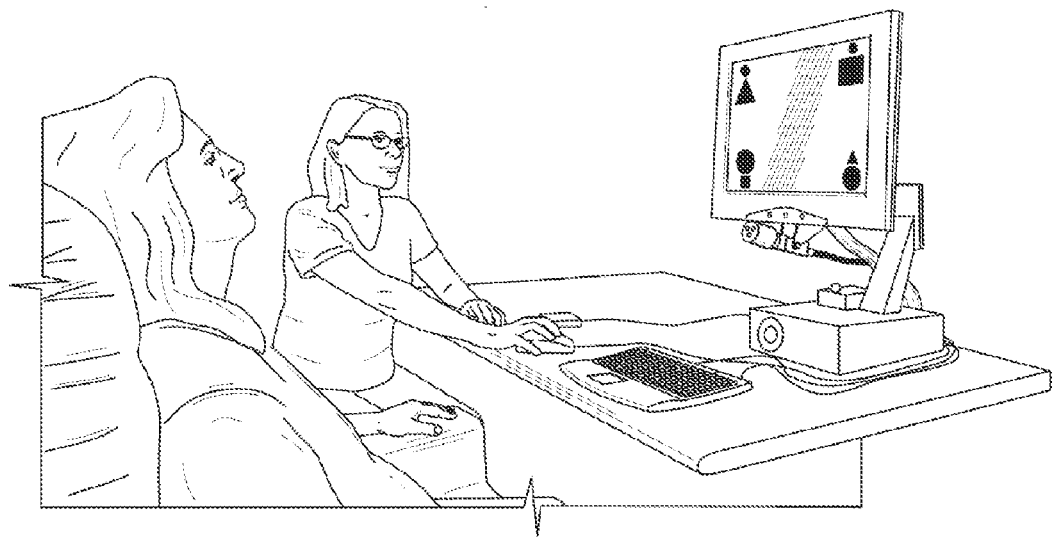
FIG. 1 is a perspective view illustrating a patient seated in front of a computer monitor during testing using the eyetracking methods of the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

I. Testing Linguistic Comprehension Using Eye Tracking

Figure 5:
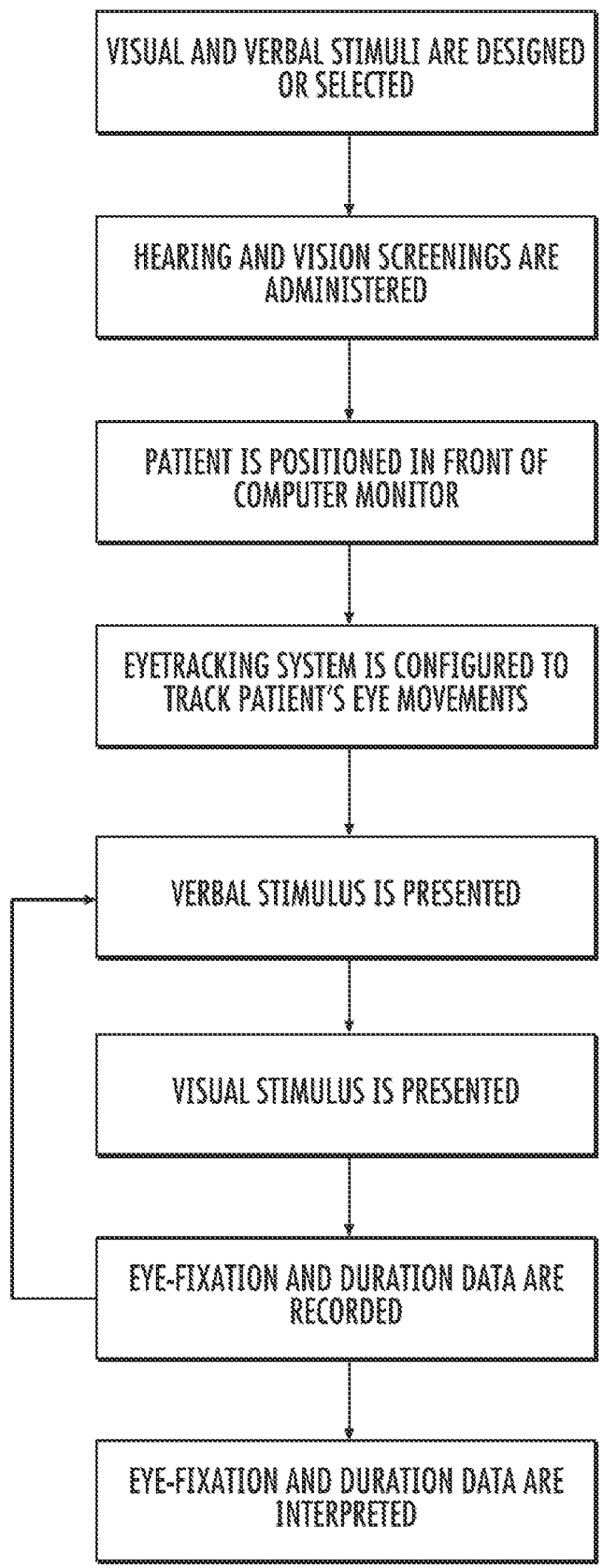
FIG. 5 is a flowchart illustrating a broad embodiment of the method for testing linguistic comprehension of the present invention.

Referring to the first step of the inventive method for assessing a patient's linguistic comprehension using eye tracking set forth in FIG. 5, a patient to be tested is preferably required to pass a vision screening to demonstrate appropriate acuity for reading text on a computer monitor at a distance of about 20-30 inches, with the exact distance dependent upon the size of visual stimuli that will be presented to the patient during assessment tasks, as will be described in detail below. Glasses or contact lenses can be used if necessary for corrected vision. The patient is preferably also required to pass a hearing screening to demonstrate appropriate acuity for 500-, 1000-, and 2000-Hz pure tones at 25 dB HL. If the patient fails to pass the visual or hearing screenings, he or she is preferably excluded from further testing or the procedure is modified to accommodate the disability. It is contemplated that other methods for screening the vision and hearing of the patient, as well as methods for testing the physical and/or neurological condition of the patient, can additionally or alternatively be administered. For example, additional screening methods may include a standard central visual acuity screening, a color vision screening, a peripheral visual acuity screening, screening for intactness of the patient's retina, a pupilary examination, ocular motility testing, and an examination of the patient's eyes for swelling, redness, drainage and lesions that may interfere with eye tracking (described below).

Next, the patient is positioned in front of a conventional computer monitor in a comfortable, seated position as shown in FIG. 1. A conventional eye-tracking system is then configured to monitor the patient's eye movements as the patient looks onto the screen of the computer monitor. The eye-tracking systems used during trials of the inventive method were an ISCAN RK426 and an LC Technologies Eyegaze system, both of which are remote pupil center/corneal reflection systems. These systems entail the use of a near-infrared light shone on one of the participant's eyes. Two points of the light's reflection on the eye, one from the pupil and the other from the cornea, are recorded via an analog video camera (located below the computer monitor in FIG. 1) with a sampling rate of 60 Hz. The video signal is then digitized, enabling a vector calculation of the eye position relative to the visual display based on the two points of reflection. Calibration procedures involve a patient viewing a series of five or more blinking dots on the screen from a distance of 34 in. from the monitor. The eye-tracking system compensates for minor head movements via a pan-tilt lens unit and therefore does not require head restraint or any form of contact between any of the components of the eye tracker and the participants.

It is contemplated that various other eye-tracking systems can alternatively be used to carry out the steps of the inventive method described below. Such systems include fixed-head systems that restrain a patient using a head or chin rest and a bite bar, head-mounted systems that correct for head movement and that may allow for general movement of a patient's body, and remote eye trackers for which hardware does not come in contact with a patient's eye or head and that incorporate pan-tilt cameras for correcting for head movement (as with the ISCAN system described above).

In selecting an appropriate eye-tracking system, it is important to consider the requirements of the system in relation to the needs of patients being tested. For example, some systems require a fixed head position to separate eye movements from head movements for high spatial accuracy. Such systems would be appropriate for young, healthy adults, who are highly cooperative and would tolerate restraints to restrict head and chin movement and use a bite-bar to help fix the head. These systems, however, may not be tolerated by adults with physical or cognitive impairments, some older adults or very active young children for whom remote eye-tracking systems may be more appropriate.

Good head control is another consideration, however, and if participants are unable to tolerate a fixed-head system, then a head-mounted (or a remote system that corrects for head movement) may be required. If patients must wear helmets or other headgear unrelated to the testing process, this may limit the use of head-worn hardware. The use of eyeglasses also must be considered: For some systems reflections from eyeglasses interfere with performance accuracy. In fact, data collection with some individuals may be difficult on any system if individuals have problems coordinating the movements of their eyes, blink excessively, or produce irregular eye movements that interfere with data collection.

Eye-tracking systems that are unobtrusive, such as remote systems, may be preferable in some natural settings, but with less physical control, the experimenter sacrifices spatial measurement accuracy. If the experimental task can be executed with little or no movement and participants are alert and cooperative, then it may be preferable to explore systems used with chin rests or other restraints to limit head movement.

Furthermore, different eye-tracking systems differ in the amount of time required to position and adjust system-related hardware. For example, if a particular system requires the use of a bite bar, this will add time to the set-up. If portability is required, it is a good idea to consider a system that could be installed on a cart that may be moved to different lab areas. Some systems operate best under special lighting conditions and the luminance levels must be considered. Typically, incandescent light (generated by standard light bulbs) contains some infrared components and may degrade performance accuracy.

Figure 2:
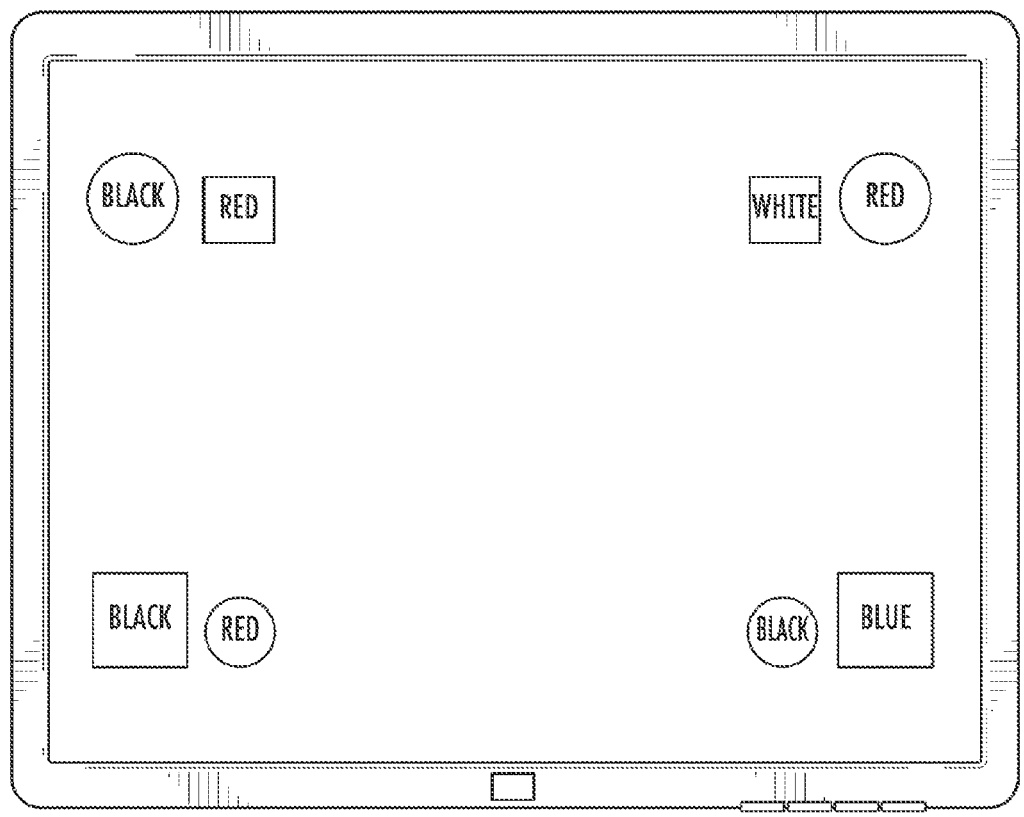
FIG. 2 is an illustration of a sample visual stimulus used in the method for testing linguistic comprehension of the present invention.

Referring again to FIG. 5, the next step of the inventive method is dependent upon whether the patient's linguistic comprehension is to be assessed on the basis of verbal comprehension or on the basis of reading comprehension. If linguistic comprehension is to be assessed on the basis of verbal comprehension, a clinician initiates a first comprehension assessment trial by simultaneously providing the patient with a pre-recorded verbal stimulus and presenting the patient with an associated visual stimulus on the screen of the computer monitor. For example, the verbal stimulus might be "the big black square is to the left of the little red circle," presented with the associated visual stimulus shown in FIG. 2 (note that the objects shown on the screen in FIG. 2 are displayed to a patient in color, and that the color words in FIG. 2 are provided for the benefit of readers of this black and white text only).

The visual stimulus includes four separate images positioned in the four corners of the screen. One of the images is a "target" image that directly corresponds to the verbal stimulus. For example, the image in the lower left corner of the screen shown in FIG. 2 is the target image based on the associated verbal stimulus "the big black square is to the left of the little red circle." The other images on the screen are "non-target" foils that are carefully controlled in terms of complexity and degree of semantic relationship with the verbal stimulus. The patient is preferably instructed to "look at the images on the computer screen in whatever way comes naturally." The visual stimulus is preferably presented for twice the duration of verbal stimulus, plus two seconds, rounded up to the nearest second, although it is contemplated that other durational relationships between the visual and verbal stimuli can be incorporated.

Custom computer software runs the experimental protocol described above, including initial calibration of how much movement of the patient's eye corresponds to specific known degrees of visual angle and presentation of the stimuli. Additional custom software allows analysis of raw eye-fixation measures (i.e., x/y coordinates corresponding to where a person's eye is focused on the computer monitor), first by determining which data correspond to actual eye fixations on the screen (i.e., stability of the eye for a long enough time to enable a person to attend to and see visual information corresponding to the image that he or she is fixating, defined herein as stability of the eye for a minimum duration of 100 milliseconds with a visual angle tolerance of 4 degrees vertically and 6 degrees horizontally) and then by determining the duration of each fixation and the corresponding area of interest (e.g., a quadrant containing a stimulus image) within the visual display with which each fixation is associated. Images within the visual stimuli are preferably positioned 20 degrees apart from one another to eliminate the possibility of clear identification of the stimulus items via peripheral nonfoveal viewing.

With a testing protocol designed to ensure the validity of the eye-mind assumption, which states that viewers tend to look at objects or images that they are thinking about, the proportion of the duration of the patient's total visual fixation time that is allocated to the target has been found to be a reliable indicator of whether or not he or she understood the verbal stimulus, and therefore provides an accurate measure of the patient's level of linguistic comprehension. A plurality of assessment trials similar to the trial described above are preferably administered to the patient in series with verbal and visual stimuli of varying complexity. Additional measures may also be used to capture the patient's comprehension response and also the degree of comprehension difficulty the patient may experience with a given item.

Figure 3:
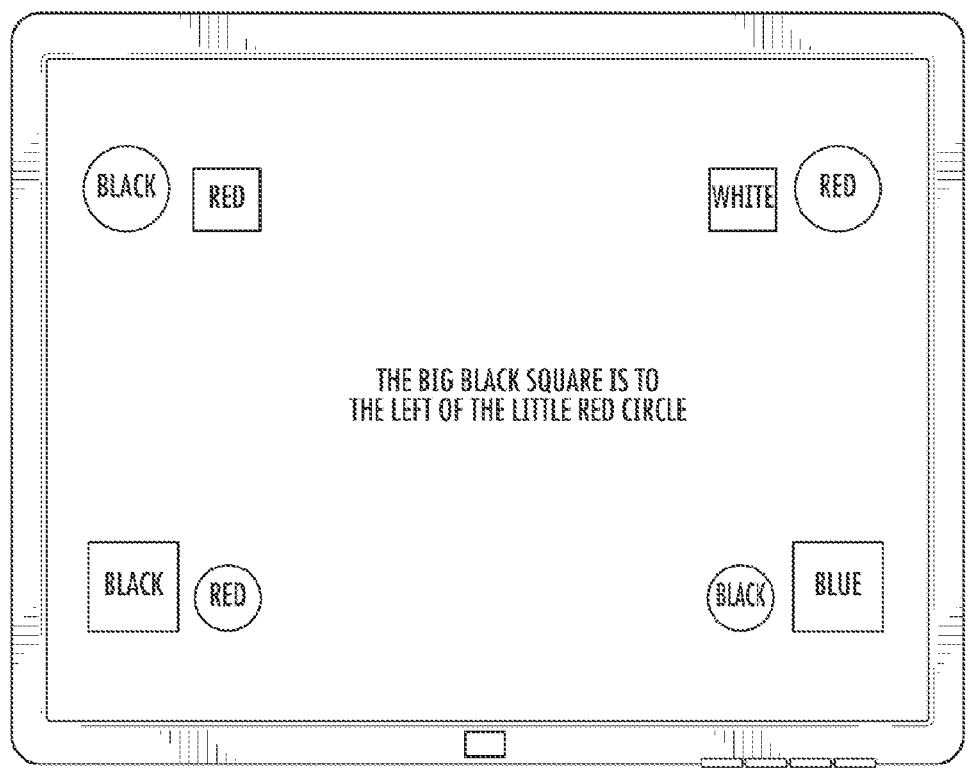
FIG. 3 is an illustration of a sample visual stimulus used in the method for testing linguistic comprehension of the present invention wherein a verbal stimulus is presented textually.

If the patient's linguistic comprehension is to be assessed on the basis of reading comprehension instead of verbal comprehension, assessment trials are administered in a substantially identical manner to that described above except that textual stimuli versions of the verbal stimuli are presented to the patient in the center of the visual stimuli displays (see the example in FIG. 3) and the auditory verbal stimuli are omitted. A patient is simply instructed to read the text displayed in the middle of the screen, and the patient's eye fixations are recorded and assessed in the manner described above.

Figure 4:
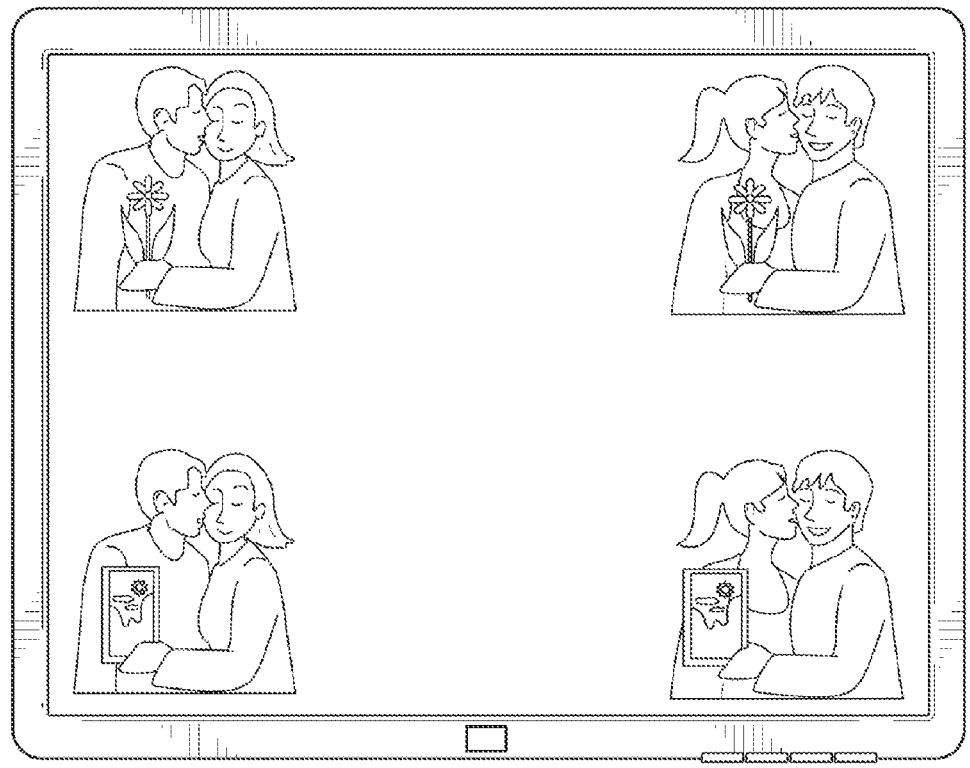
FIG. 4 is an illustration of an example of a second type of visual stimuli used in the method for testing linguistic comprehension of the present invention.

The stimuli presented to a patient during either form of comprehension assessment testing (i.e., verbal or reading) are preferably selected from two general groups of stimuli: 1) those that include the recitation and depiction of varying shapes, colors, sizes, and prepositional and directional terms (such as in the example described above and shown in FIG. 2) which are considered relatively "culture free" stimuli because they do not require patients to understand culturally specific or unfamiliar words, or to interpret images of objects or actions with which participants may not be familiar; and 2) those that include the recitation and depiction of multicultural and multigenerational representations and common terms used in everyday communication. An example of a stimulus from the second group is shown in FIG. 4. Note that the physical stimulus features and semantic content of each image in the stimulus are carefully controlled so that no image distracts the viewer more than any other when no verbal stimulus is presented. There are four potential verbal stimuli for this item: "the man is kissing the woman who is holding a flower"; "the woman is kissing the man who is holding a flower"; "the man is kissing the woman who is holding a picture"; "and the woman is kissing the man who is holding a picture."

Images associated with the first group of stimuli described above are based on an adaptation of the Revised Token Test (RTT). The RTT is a standardized test for the assessment of auditory comprehension for adults with neurogenic language disorders in which patients are given verbal commands to touch or manipulate plastic tokens that vary in color, shape, and size. An example of a simple command is "Touch the green square". An example of a more complex command is "Put the blue circle to the right of the green square." Responses to each element of each command are scored on a 15-point multidimensional scale. To create the stimuli in the first group, the verbal stimuli from the first eight subtests of the RTT were modified. Five items were created for each of the eight subtests. Across subtests, verbal stimuli vary in length and complexity. Verb phrases such as "touch" and "put" were eliminated. As in the RTT, squares and circles are used as shapes; black, green, red, blue, and white are used as colors; and big and little correspond to the size of the shapes.

An advantage of the first group of stimuli described above is that each of an image's eight subsets has distinct linguistic stimulus characteristics, with five items available to sample repeated performance in each. Additionally, because each nontarget image within a display is controlled for complexity and degree of semantic overlap with the "target" image, gradations of comprehension, rather than just simple "correct" or "incorrect" responses, may be assessed.

An advantage of the second group of stimuli described above is that each stimulus represents a broad array of linguistic structures, from short to long and from simple to complex. Further, a stimulus from the second group entails four multiple forms, in that four distinct sets of verbal stimuli may be used with the same stimulus set.

Verbal stimuli used in conjunction with visual stimuli such as those described above are carefully developed to assess a wide array of single words and simple and complex sentences. During trials of the inventive method, the selection of linguistic constructs represented by the verbal stimuli was based on a detailed review of items within a broad range of aphasia assessment instruments used in current clinical practice. Two hundred and thirty-two verbal stimuli were designed in groups of four, to correspond to four visual stimuli in multiple-choice displays. There were 58 sets of four verbal stimuli. Verbal stimuli ranged from single words to complex sentences and combinations of sentences. Single word stimuli included nouns within the same semantic category, nouns representing superordinate semantic relations, nouns representing subordinate semantic relations, nouns having auditory/phonetic similarity, adjectives, verbs, and numbers). Phrases included noun and noun combinations and multiple digits. Simple canonical sentences include subject-verb-object sentences with animate noun subjects and with pronoun subjects, with transitive verbs (having a direct object) and intransitive verbs, and with prepositions and objects of prepositions. Grammatically complex sentences included statements with reversible subjects and objects in past and present tenses and reversible comparative adjectives. Other sentences included quantity statements, descriptive sentences, statements about opposites, negative statements, descriptive statements in past tense, and cause-and-effect statements. Two-sentence combinations included statements about related sequences of events. The following controls were implemented within each set of four verbal stimuli: similarity in length (number of letters, phonemes, syllables, and words), similarity in frequency of occurrence in English according to norms by Kucera and Francis (1967) and by Thorndike and Lorge (1944), and word familiarity according to norms by Dale & O'Rourke (1981). The detailed rationale for the selection of these metrics to guide verbal stimulus design and a summary of the strengths and weaknesses of these and other verbal stimulus control measures was considered in great detail. Verbal stimuli were prerecorded using a male voice (for improved perception by older adults more likely to have high-frequency than low-frequency hearing acuity problems) and digitized.

An alternative embodiment of the comprehension method described above is contemplated in which a clinician display screen is additionally incorporated to help a test administrator monitor and evaluate the progress of assessment as the assessment proceeds in real time. The clinician display is a second screen seen only by the clinician and not by the patient being tested. The display shows the same display seen by the test participant, but also includes current on-line eye tracking and test-scoring information. Video images of the patient's eyes indicate whether the eye-tracking functions are working correctly. A moving dot with a short "tail" represents the patient's gaze trace activity, both on and off the screen. If the patient looks off the screen, the gaze point indicator dot changes color (and appears on the clinician's screen at the nearest location to the patient's real gaze direction). A different visual indicator alerts the clinician if the patient closes his eyes.

In addition to showing the patient's eye movement patterns, the clinician display screen shows the results of automated scoring. The display shows both intermediate results during the test and the final results immediately following the test. The clinician display screen thus provides a powerful user interface for allowing the test administrator to respond to eye tracking and scoring information and control test progress. A simple set of graphical touch screen controls allow the administrator to easily and quickly start, pause, adjust, resume, and stop program operation.

A. Design of Stimuli

It is contemplated that stimuli other than the types described above can be administered during testing, although it is critical that special consideration be given to the selection and/or design of such stimuli to ensure accurate assessment. Attentional impairments may affect not only the accuracy and efficiency of an individual's language comprehension skills, but also the accuracy and efficiency of the selection of an appropriate multiple-choice response. Viewers may be distracted by bottom-up processes of which they are unaware. For example, it is possible that a participant understands a verbal stimulus and identifies the correct corresponding visual stimulus, but becomes distracted by the physical features of another stimulus (a non-target foil) so that she or he selects the distracting stimulus instead of the correctly identified one. In such a case, accurate comprehension of the verbal stimulus would not be captured in the "incorrect" score the participant would receive for that item. Consideration of the influences of stimulus features and image content on test responses of patients with neurogenic communication disorders is especially important.

It is impossible to predict the influence of visual image characteristics on a particular individual's performance; the only way to reduce their influence on performance for any given individual is to control for image characteristics in the design of multiple-choice image sets. Strategic design of specific physical stimulus characteristics in multiple-choice images is thus essential to the validity of responses to those images during testing. Items that do not share the same basic visual characteristics as all other items in the perceptive field may attract disproportionate attention. This phenomenon is referred to as the "pop-out" effect. Features of multiple-choice images in a display evoke the pop-out effect when the viewer's visual attention to specific images becomes disproportionately allocated across presented images. For instance, colored images mixed with black and white images may attract greater visual attention. Physical stimulus characteristics and semantic content conveyance features with demonstrated effects on visual attention include color, scene context, orientation, imageability, size, viewpoint, depth cues and shading, image familiarity, luminance, concept frequency, complexity, social and cultural influences, symmetry and asymmetry, and clarity. Each of these characteristics, if not controlled for across sets of items in a multiple-choice display, may evoke the pop-out effect during multiple-choice assessment tasks. Empirical evidence regarding each of these characteristics is summarized below.

B. Visual Stimulus Characteristics and Effects on Disproportionate Visual Attention Color: Color functions as a distractor in image-based tasks. Colored items attract more immediate and longer attention when presented along with black and white items, or items that significantly differ in color. Deffner (1995) conducted a study of image characteristics considered critical in image evaluation. Participants were shown a series of images and were instructed to express their preferences regarding image quality. Color saturation, color brightness, and color fidelity were all items shown to influence how participants viewed images.

Orientation: If a single item within an image has a different orientation from other items within that image, the item with the differing orientation becomes salient. The same effect occurs if one object presented in a multiple-choice display has a different orientation. The viewer's visual attention might be influenced by the different orientation of the object, and he or she looks more often and longer at this image than at the other images with the homogeneous orientation. The pop-out effect has been shown to decrease if there is more than one item with a different orientation.

Size: When viewing multiple images within one display, relative size is a physical property of images that influences scanning patterns. The size of a stimulus refers to the spatial extent of the item. The disproportionate size of an object is likely to attract disproportionate attention to images within a multiple choice display. The viewer is more likely to focus on the biggest or the smallest object in a display of several images.

Depth cues: Shading, highlight details, and shadow contrast have been shown to influence eye movement patterns when viewing images. Individuals allocate more attention to visual stimuli cued in depth through shadows, for instance, than to two-dimensional stimuli without depth cues. Disproportionate looking at a multiple-choice image display occurs when two dimensional images and images with depth cues are displayed together.

Luminance: Barbur, Forsyth, and Wooding (1980) found that background color and luminance have an impact on viewers' visual scanning patterns. In their study numbers were recalled better using a middle-grey background instead of a black one. The correct performance of tasks also increased when the luminance of the background was greater than one-third of that of the target. Additionally, contrasts in luminance have been demonstrated to be recognized faster and also with higher frequency than changes in motion and complexity. Different degrees of luminance of images may cause a disproportionate distribution of eye movements in multiple-choice displays. Likewise, luminance differences between the backgrounds of the images can influence the viewer's visual attention as well.

Complexity: Eye movement patterns differ depending on the complexity of images one is viewing. Consequently, having different levels of complexity across individual items within a display may result in differential visual attention, as measured by eye movement patterns allocated to those images, regardless of the content of an accompanying verbal stimulus. When viewing complex shapes, viewers tend to focus on familiar geometrical shapes within them. Bozkov, Bohdanecky, Radil-Weiss, Mitrani, and Yakimoff (1982) showed that viewers fixate the angles of figures (polygons) when they are instructed to identify their shapes. According to these authors, "the existence of converging line segments of the polygonal contour shapes are an important cue for form perception and eye movement guidance". Disproportional visual attention in a multiple-choice display is likely when the shapes of the presented polygons include different amounts of converging line segments and angles. Recognition time varies, depending on how easily the complex shapes of the objects can be recognized as familiar geometrical concepts. The complexity of the shape of an object has an impact on a viewer's visual attention. For instance, a circle is more easily recognized than a shape of a combined polygon and a circle. Viewers tend to focus longer on complex shapes than on simple ones.

The frequency and size of saccadic eye movements and corresponding fixations differ according to the content of images viewed. While viewing a complex natural scene, the duration of individual fixations decreases while the number of eye movements increases. The opposite effect is observed while watching simple patterns, such as dots, squares, and lines. If the complexity of the images in a multiple-choice format differs among the images within a display, the proportion of fixation duration allocated to images within the display may be imbalanced. More fixations and greater total fixation durations may be observed on complex images than on simple ones.

Symmetry: Symmetry is identified during the first few fixations within a visual scan, and has a strong influence on the subsequent scan patterns. Because redundancy is inherent in symmetry, visual attention, as indexed by eye fixations, is often allocated primarily to one side of the symmetric shape. In contrast, while scanning asymmetric stimuli, eye fixations tend to be distributed widely over the stimulus. Thus, symmetric figures are recognized more easily and faster than asymmetric ones. Disproportional distribution of visual attention may result when a different degree of symmetric and asymmetric forms are displayed in images in a multiple-choice format.

Clarity: The time a viewer spends fixating on images tends to be greater when the image is blurred than when it has clear boundaries. If images in a multiple-choice display have different grades of clarity, the viewer is likely to fixate longer on the most blurred image such that the distribution of eye fixations would not be balanced among images within the display.

Scene context: According to Boyce and Pollatsek (1992), "scene context contains geometric as well as semantic information that operates on the identification of objects". They found that participants fixate longer on objects that do not belong in a specific context, for instance a bathtub in a living room. The background or context has an impact on accuracy of identification of objects. If participants are shown images with targets in a typical context, then it is easier to identify them, compared to when they are presented without context. Disproportionate looking may be evoked when the context of images within a display is not controlled. For example, if some objects in multiple-choice displays are shown in isolation while others are shown within a scene context, the distribution of fixations is not likely to be balanced among the isolated objects and the images with scene contexts. Likewise, if one object is displayed in an unusual or inappropriate context, the viewer might need more time to identify the object accurately and a disproportionate distribution of eye fixation might occur as well.

Imageability: "Imageability" refers to the ease and accuracy by which a semantic idea is conveyed by a visual stimulus. It corresponds to the notion of abstractness versus concreteness of a depicted concept. If one or more of the target images within a display are not "imagable", this may influence where a person looks within a display. For example, it is harder to represent the abstract concept of "angry" than to represent the concept "flower" or "ball"; the image for "angry" may disproportionately attract a viewer's attention when shown along with images of a flower and a ball. The imageability of concepts is said to underlie the finding that objects are recognized faster and at higher rates than actions when controlling for physical stimulus features. The authors' interpretation for these results is that stationary objects, such as a chair or lamp, are easier to distinguish from one another, whereas actions look similar. If varying stimulus categories are presented in a multiple-choice format, disproportional looking can be evoked because one category may be more easily recognized than the other, and visual attention is therefore likely to be distributed differentially.

Perspective: The viewer's point of view has been demonstrated to influence recognition of an object. For instance, a familiar object, such as a cup, might be harder to recognize within a display when the viewpoint is from above the cup, as opposed to the front of the cup. Disproportionate allocation of visual attention may occur if one object in a multiple-choice display is represented in an unusual perspective in contrast to the other objects.

Concept familiarity: The fixation time on the visual stimulus may increase dramatically when the stimulus is not familiar to the viewer. Rayner et al. (1989) found similar results when observing the reading of unfamiliar words. This phenomenon must be considered especially with regard to the viewer's social and cultural background. His or her semantic knowledge might not be equal for all concepts represented by the images in a multiple-choice display.

Concept frequency: Concept frequency is a construct representing the frequency with which an individual encounters a particular concept in everyday life. The construct parallels in the cognitive domain what word frequency represents in the linguistic domain. Rayner et al. (1989) observed effects of word frequency on eye fixations during reading. The ease or difficulty in processing a word is reflected in the fixation time on this word while reading. The fixation time depends not only on the number of syllables in a word but also on the word's predictability. Compared to high-frequency words, low-frequency words tend to be fixated longer. Although word frequency and concept frequency are not identical, objects representing concepts that correspond to low and high-frequency words shown together within a display are likely to cause disproportional viewing patterns.

For the purpose of directly complementing linguistic stimuli, each visual stimulus in comprehension assessment ideally represents a prototypical image of the semantic content it is intended to convey. This presents several social and cultural challenges due to individual life experiences. For instance, a sari is not a prototypical image of clothing in western European and northern American cultures, but it does represent prototypical clothing in eastern Indian cultures. Furthermore, if a linguistic assessment task contains a picture of a computer mouse and the viewer has never heard of a computer mouse, but the other images within the display represent familiar objects, the viewer may allocate more attention to the unknown object as compared to the other items within that display.

II. Testing the Effect of Semantic Associative Priming Using Eyetracking

Figure 6:
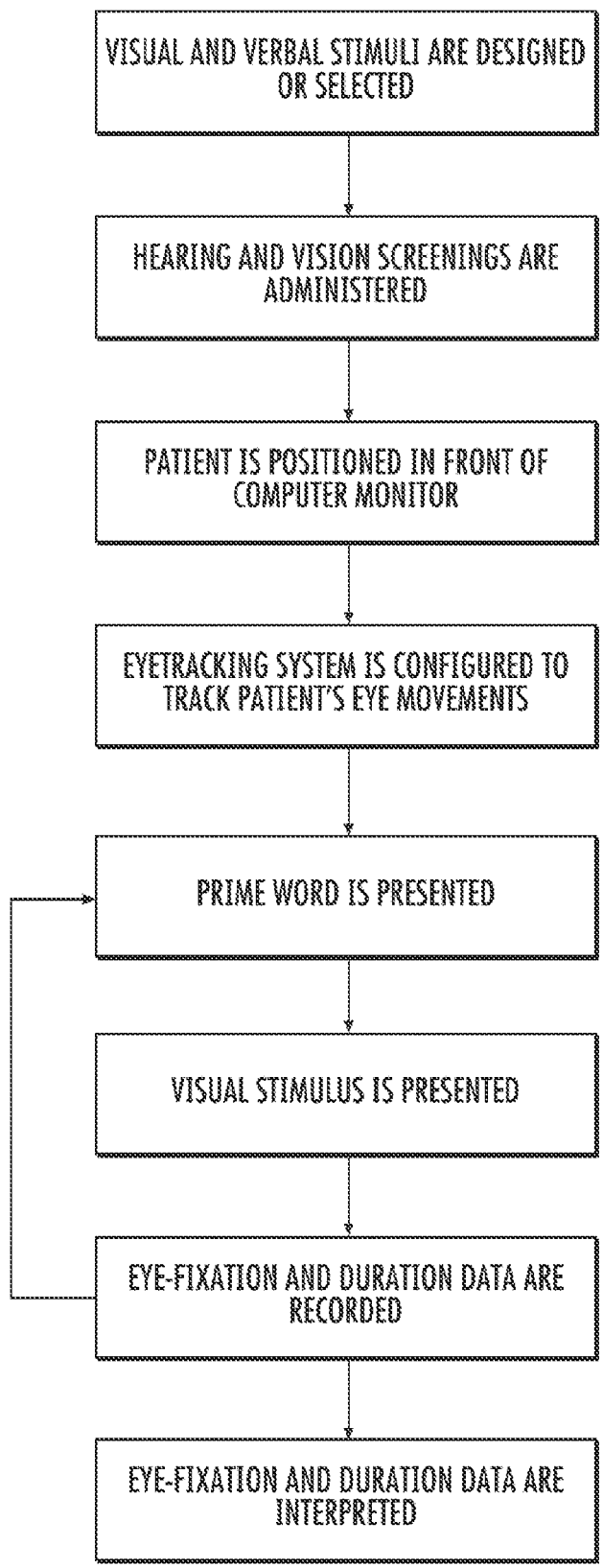
FIG. 6 is a flowchart illustrating a broad embodiment of the method for testing semantic associative priming of the present invention.

Referring to the first step of the inventive method for assessing the effect of semantic associative priming on a patient using eye tracking set forth in FIG. 6, a plurality of picture stimuli and corresponding high-association prime words must be designed. Alternatively, necessary stimuli can be selected, such as from a predesigned set of stimuli provided as part of a computer software bundle. The method used to develop such pairs of stimuli and corresponding highly-associated prime words for experimental trials of the inventive method will now be described in detail.

A. Picture Stimuli

Picture stimuli originally tested in the stimulus development process consist of 260 gray-shaded object pictures adopted from the largest online picture databank available for experimental and clinical studies, at the Tarr Laboratory Web site, Cognitive and Linguistic Sciences Department, Brown University. Rossion and Pourtois (2004) have established normative data for naming agreement, familiarity, complexity, and imagery judgments for these stimuli, which are modified versions of the 260 line drawings developed by Snodgrass and Vanderwart (1980). All the pictures were uniformly sized to 450×450 pixels with 300 pixels/in. resolution.

B. Prime-Target Pairs

A total of 100 adult, college-age native speakers of English (age range: 18 to 26 years; M=19.8, SD=2.4) who reported normal language abilities served as participants for the purpose of assigning associated words to the pictures. The participants were recruited from the participant pool of the Ohio University Department of Psychology and given extra credit points for their participation. All the 260 picture stimuli were presented in booklet form to each participant. They were instructed to write the first word they thought of when seeing each picture in the booklet.

The responses to each picture stimulus were noted and tallied across participants. The response frequency (number of participants choosing the same association word for a particular picture stimulus) range for the 260 picture targets was from 2% to 81% (M=45.73, SD=20.12). A response frequency of 25 (1 SD below the mean) was set as the cut-off criterion. Of the 260 picture stimuli presented, 95 were excluded because they received variable responses, defined as a response frequency of less than 25 for the highest frequency response. An additional 36 picture stimuli were discarded because they shared their highest frequency response words with other pictures in the set for which the same responses were more robust. A total of 129 picture targets along with their high frequency response words were selected. The response words assigned as associative words to the picture stimuli were designated as semantically associated primes for the corresponding 129 pictures. Given that priming is unidirectional for certain word pairs, there is a risk in using these associative responses as primes and not as targets. For instance, guitar may prime music, but music may not necessarily prime guitar. In this case, the use of the response music as a prime for guitar is questionable. This issue was addressed by testing every prime for a significant priming effect on its corresponding target using the traditional naming priming method.

C. High-Association Targets and Low-Association Nontarget Items

In the eye movement condition (Phase II), semantic (associative) priming was studied using a multiple-choice format. Each visually presented word prime was followed by a set of three pictures, one of which had a high association with the prime (target item) and two of which had a low level of association with the prime (nontarget items). To determine which two pictures adequately qualified as low-association nontarget items to the prime, the following steps were taken:

1. Using a random number table in which each number corresponded to a picture stimulus, five pictures were chosen as possible choices for the selection of two low association nontarget items for each prime word.

2. To ensure that these pictures randomly assigned as low-association nontarget items were, in fact, not related to the prime, word association norms provided by Palermo and Jenkins (1964) were used. For each prime word, none of the five pictures assigned as nontarget items could correspond to words given as responses in the norms. If any of the five choices had been given as responses to the corresponding primes, new picture targets were selected from the random number table.

3. To check the degree of nonassociation between the prime and the targets and to select the final two nontarget items for each prime word from a possible choice of five, the list of nontarget pictures corresponding to each prime word was given to 20 additional adult native speakers of English with normal language abilities. Participants were recruited via flyers from the Ohio University student community and were in the age range of 18 to 25 years (M=20.22, SD=0.91). These participants rated the degree of association between the prime word and each of the five pictures selected as low-association words on a 6-point rating scale ranging from 0 (no association) to 5 (medium association). The two picture stimuli with the lowest ratings (2 or lower) were designated as the two nontarget low-association items for a particular prime word. For each prime word, the following image array would include one target image along with two nontarget foils. The two nontarget foils were the pictures selected to have lowest association to the prime word from this stage of the experiment. The nontarget foils were not used for the traditional priming experiment but only for the eye movement phase.

D. Traditional Priming Experiment with Prime-Target Pairs

To ensure that the above pairs of related stimuli led to semantic (associative) priming effects, a traditional semantic priming task was conducted with 20 additional participants selected using the criteria mentioned in the Prime-Target Pairs section and recruited via flyers from the Ohio University student community. The age range for these participants was between 18 and 22 years (M=19.60, SD=0.88). Participants were tested individually. Each participant was presented with all of the picture targets along with their corresponding names on a computer screen one at a time and was asked to read these names aloud. This was done to ensure that participants were familiar with the names of all the pictures. For each participant, two sets of trials were then conducted. During the first set, each of the picture targets was preceded by an unrelated prime. For the next set of trials, each of the targets was preceded by a related prime. This method was followed to obtain a within-participant comparison for the related versus the unrelated trials. The order of presentation was held constant across the two sets of trials. This was done so that any extra facilitation in responding to the target items in the second trial as a result of prior exposure to those items during the first trial was constant across items.

All stimuli were presented by means of Media Lab software in the center of the computer screen. Each related prime-target trial consisted of (a) presentation of a cross mark for 100 milliseconds, (b) presentation of the prime word (for related trials) or unrelated word (for unrelated trials) in lowercase letters in Arial font for 400 milliseconds, (c) presentation of a single target picture to be named in the center (size: 450×450 pixels, resolution: 300 pixels/in.) until a response was obtained, and (d) initiation of next trial after a 2-s delay initiated at the beginning of each response. Participants were asked to concentrate on the middle of the screen and to name as rapidly and accurately as possible the depicted object when it appeared into a Plantronics Audio 310 over-the-head noise-canceling boom microphone. They were asked not to use overt fillers such as "um" or "er" during the naming task so as not to trigger inaccurate verbal response time measures. The microphone was connected to the computer for automatic recording of voice response times for naming. The experimenter sat in the same room as the participant to monitor responses.

E. Stimuli Analysis

Response times for naming each picture target with the prime and with the unrelated word across participants were compared using a total of 129 paired t tests. All inaccurate response data (15.4%) were deleted from the database. Of the inaccurate data, 5.7% were a result of microphone-related errors. The remaining 9.4% were deleted because they represented inaccurate names of targets. Of the 129 prime-picture pairs, only 50 pairs showed significant reduction in naming time in the related prime condition in comparison with the unrelated word condition (a≤0.01).

Reaction time facilitation observed for only 50 prime-picture pairs and not all 129 pairs is indicative of the fact that repetition priming for pictures used in both the related and unrelated trials can be ruled out as a priming effect. The reason for the semantic (associative) priming effect being limited to only 50 prime-picture pairs could be due to reversal of prime and target in this experiment as compared with the free-association task mentioned above. To clarify, the written words used as primes in this experiment were, in fact, generated as targets in response to the pictures in the initial free association task. Hence, although the pictures primed the written words in the free-association task, the written words may not equally prime the picture in the reverse direction.

Conducting item-wise analysis for each target picture was important to select only those prime-target pairs that showed very strong evidence of the semantic (associative) priming effect and to keep the final experimental prime-target numbers for the eye movement phase small and manageable. Of the 50 pairs of prime-target pairs showing facilitation in this experiment, an additional 16 pairs were deleted because they shared low-association nontarget pictures with other item pairs. The remaining 34 prime-picture pairs were included for further experimentation.

Referring to the next step of the inventive method for assessing the effect of semantic associative priming on a patient using eye tracking set forth in FIG. 6, a patient is preferably subjected to vision and hearing screenings in the manner described above under the section titled "Testing Linguistic Comprehension using Eyetracking." Next, the patient is positioned in front of a computer monitor and a conventional eye-tracking system is configured to monitor the patient's eye movements as the patient looks onto the screen of the computer monitor, also as described in the previous section.

Next, the following instructions (or some similar variation thereof) are given to the patient: "You will see words and picture sets on a computer screen. Read the words and look at the pictures on the screen in whichever way that comes naturally to you. You do not have to remember any of the words or pictures." Next, arrays of picture stimuli and corresponding high-association prime words (developed and selected as described above) are presented to the patient on the computer monitor as shown in FIG. 7. It is contemplated that the prime words can alternately be presented to the patient in the form of prerecorded verbal stimuli. For each visually presented prime word in the center of the screen, a set of three pictures subsequently appear in three corners of the screen (size of pictures: 450×450 pixels, resolution: 300 pixels/in.). One picture in each set represents a high semantic (associative) relationship with the prime word, whereas the other two pictures represent a low association with the prime word. The position of the target and nontarget foils within each trial display is carefully controlled such that the targets and foils appeared with equal frequency in all four corners of the display over the course of successive trials.

As the picture stimuli are presented, custom software allows analysis of the patient's raw eye-fixation measures. Fixation was defined as 100 milliseconds of stable eye-in-head position with a tolerance for change in position within 4 degrees vertically and 6 degrees horizontally. A threshold of 100 milliseconds has been shown to effectively differentiate fixations from other ocular motor activities and is consistent with current physiological and cognitive models of eye movements and information processing.

Figure 8:
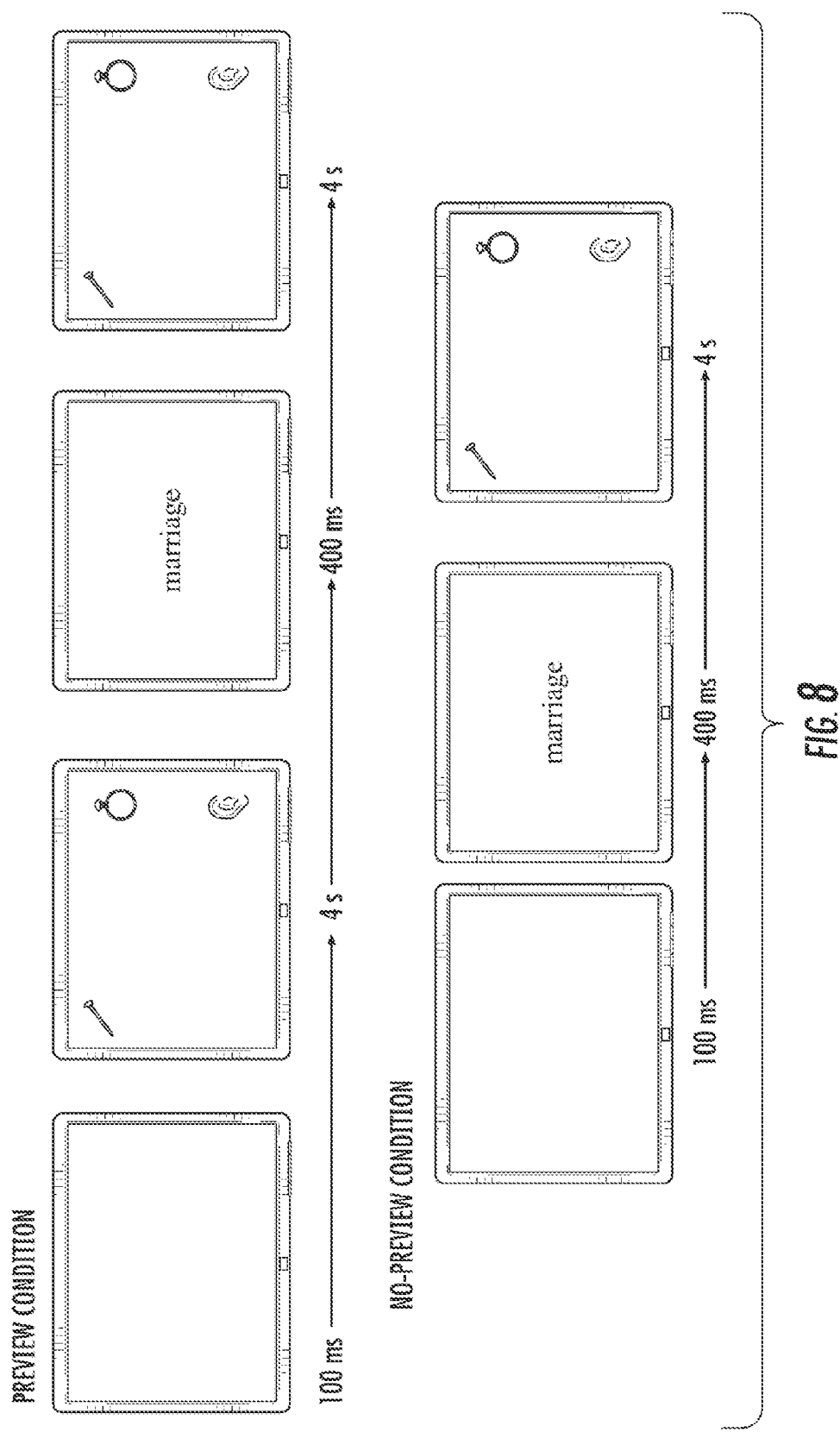
FIG. 8 is an illustration of a sample preview and no-preview trials of the method for testing semantic associative priming of the present invention.

The eye movement priming protocol consists of two possible conditions: preview and no-preview (both are depicted in FIG. 8). In the preview condition, the order of presentation of stimulus items for each trial was as follows: (a) presentation of a blank screen for 100 milliseconds, (b) preview presentation of the picture array for 4 s, (c) presentation of the prime word for 400 milliseconds, and (d) repeated presentation of the picture array for 4 s. In the no-preview condition, the order of presentation of the stimulus items for each trial was as follows: (a) presentation of a blank screen for 100 milliseconds, (b) presentation of the prime word for 400 milliseconds, and (c) presentation of the picture array for 4 s. Generally, stimulus onset asynchronies (SOAs) over 400 milliseconds between the prime and target are said to enable strategic processes in priming. At shorter SOAs (less than 400 milliseconds) automatic processes dominate.

A patient's fixation duration measures during administration of the above-described method steps, including both the preview and non-preview conditions, have been found to be a reliable indicator of the effect of semantic associative priming on the patient. Such measures include the proportion of fixation duration (the total duration for which an individual fixates on one specific area divided by the total time of all fixations during the viewing of a display), average fixation duration (the mean fixation duration for all fixations on a particular item in the display), and first-pass fixation duration on a target (the time interval between when a viewer first fixates on and first fixates away from an area of interest). Greater durations of such measures correlate with a greater effect of semantic priming on a given patient.

III. Testing Working Memory Using Eyetracking

Figure 9:
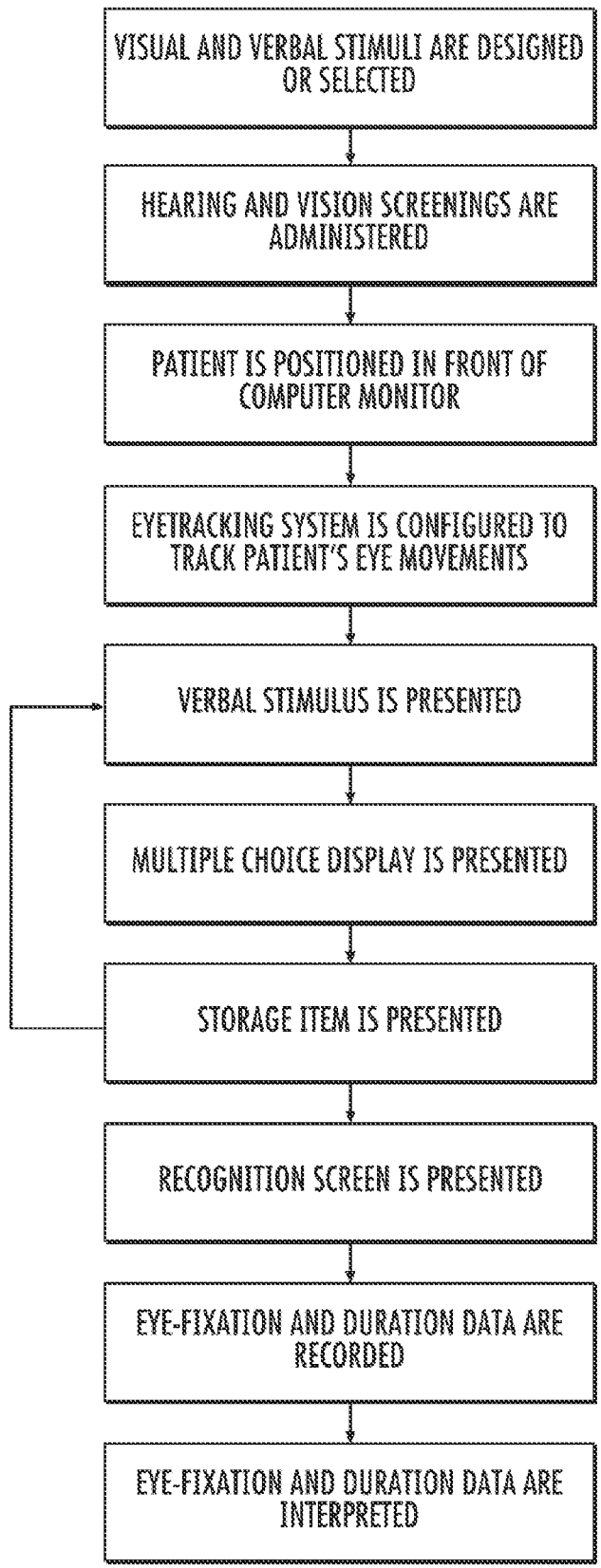
FIG. 9 is a flowchart illustrating a broad embodiment of the method for testing working memory of the present invention.

Referring to the first step of the inventive method for assessing the working memory of a patient using eye tracking set forth in FIG. 9, a patient is preferably subjected to vision and hearing screenings in the manner described above under the section titled "Testing Linguistic Comprehension using Eyetracking." Next, the patient is positioned in front of a computer monitor in a seated position and a conventional eye tracking system is configured to track the patient's eye movements as the patient looks onto the screen of the computer monitor, also as described in the linguistic comprehension section above.

Figure 10:
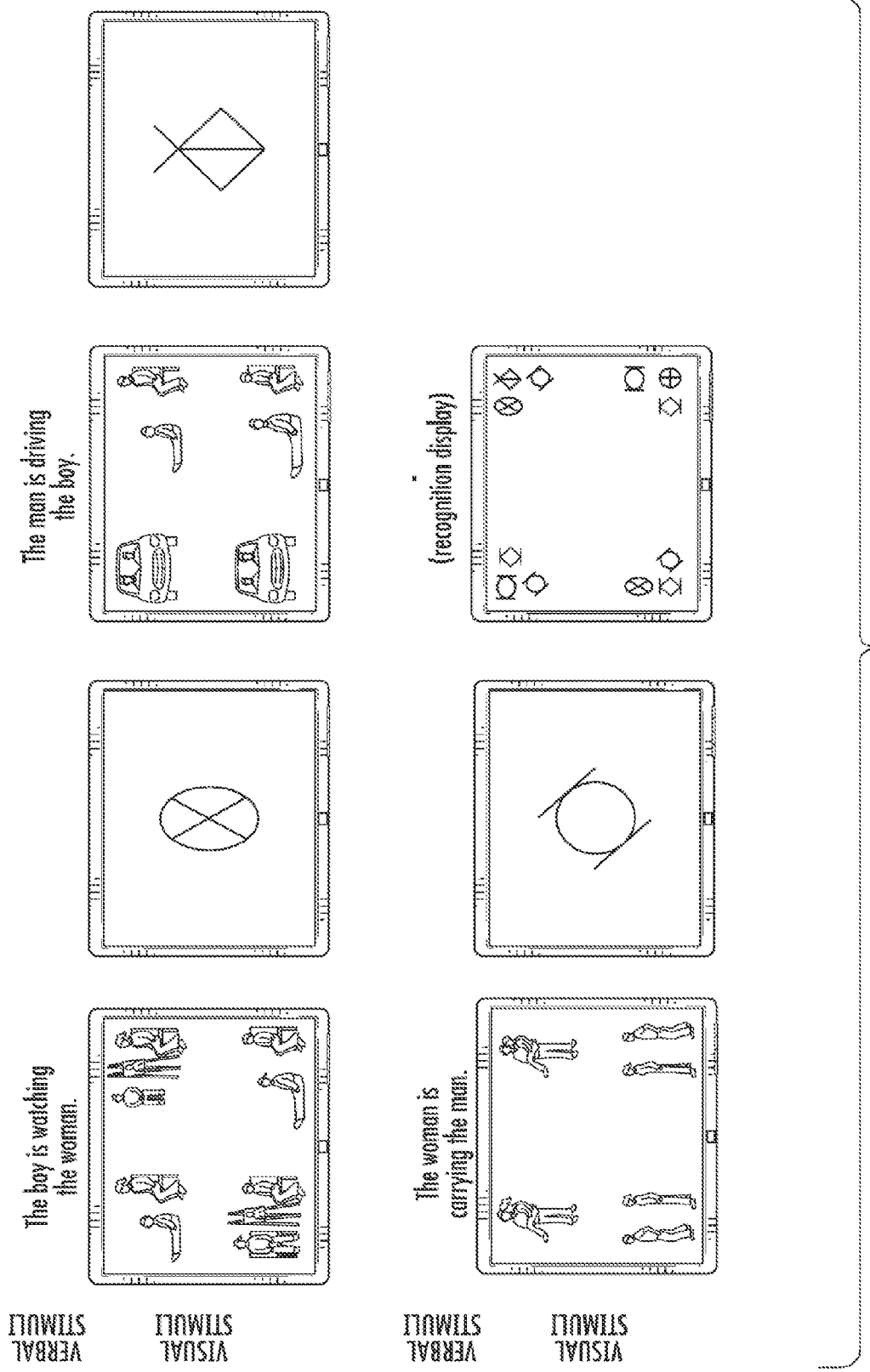
FIG. 10 is an illustration of a sample sequence the method for testing working memory of the present invention.

Next, the patient is given the following instructions (or some similar variation thereof): "You will see pictures and hear sentences. Listen to the sentences and look at the pictures. Remember the colors or shapes that you see. Then look at the corner with the colors or shapes you just saw." The patient is then presented with a multiple-choice picture array displayed on the computer monitor accompanied by a prerecorded verbal stimulus that corresponds to one of the images in the array. Referring to the array at the far left in FIG. 10, for example, the verbal stimulus "the boy is watching the woman" corresponds to the picture in the lower right quadrant of the display. Following the multiple-choice array an item to be remembered (a "storage item") is presented within a separate display. The storage item is preferably an abstract symbol or a color box. Several multiple-choice arrays, each one followed by the presentation of a storage item (color or symbol), are presented in a sequence as shown in FIG. 10. A sequence is preferably composed of between 2 to 6 multiple-choice arrays.

At the end of each sequence a "recognition screen", such as the recognition screen at the far right in FIG. 10, is presented to the patient. The recognition screen is a multiple-choice array containing various combinations of symbols or colors presented in each quadrant of the display. One of the combinations (the target) corresponds to the combination of all of the symbols/colors previously presented to the patient within a given sequence. For example, the upper right quadrant of the recognition screen shown in FIG. 10 corresponds to the preceding sequence of storage items.

The multiple-choice arrays in a sequence are preferably displayed for twice the duration of the auditory stimuli plus two seconds rounded to the nearest second because previous studies have shown that this duration provides sufficient time for recognizing and finding the correct image in cases of mild to severe comprehension deficits. Displays with storage items are preferably presented for two seconds each. Recognition arrays are preferably presented from 5 to 15 seconds each as determined by the multiplying the number of items to be recalled by 2.5 seconds. Recognition arrays are not accompanied by verbal stimuli.

Practice trials are preferably administered to assure comprehension of task instructions prior to testing. Multiple-choice arrays are preferably presented in set sizes of 2 to 6 in ascending order with two sets of each size presented. Abstract symbols are preferably used as storage items in half of the sets color boxes are preferably presented as storage items in the other half of the sets.

Custom analysis software is used to determine the patient's eye fixation locations and durations, and to eliminate blink artifacts. Fixation was defined as a stable position of the eye for at least 100 milliseconds with a horizontal tolerance of 6 degrees and a 4 vertical tolerance of 4 degrees.

Eye-tracking data are summarized in terms of the proportion of fixation duration (PFD) on target images, which is defined as the total fixation duration allocated to the quadrant with the target image divided by total fixation duration on the screen (total presentation of the stimuli minus blink artifact and duration of saccadic eye movements). The target image is defined as the image corresponding to the verbal stimulus (for multiple choice picture arrays) or the image containing all the items to be recalled (for the recognition screens). Previous research on participants with and without language impairment has shown that PFD on the target image within an array is a valid and a reliable measure of comprehension ability. In individuals without cognitive, language, and neurological impairments PFD on the target has been shown to be significantly greater than on the foils, meaning that the image corresponding to the verbal stimulus will be attended to for a longer period compared to other images within a display when comprehension of that item is possible.

IV. Testing Attention Using Eyetracking

Figure 11:
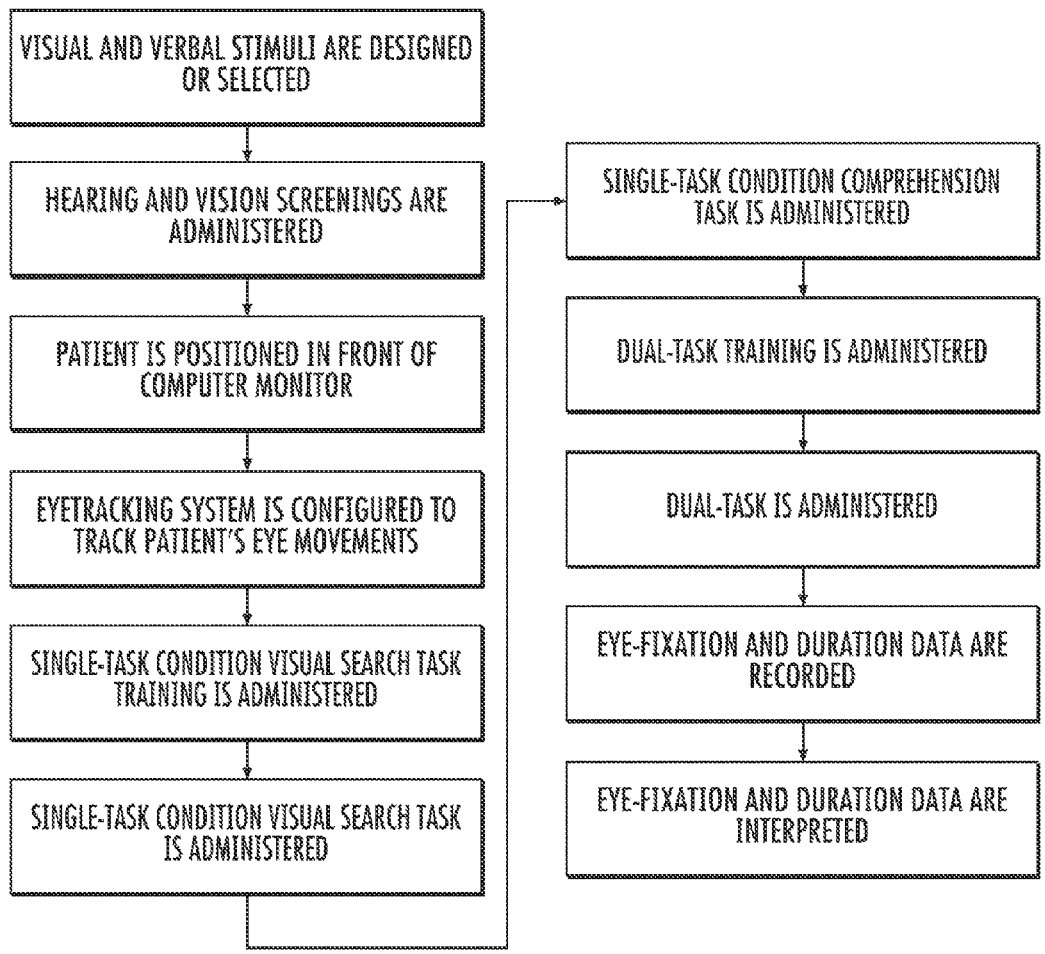
FIG. 11 is a flowchart illustrating a broad embodiment of the method for testing attention allocation of the present invention.

Referring to the first step of the inventive assessment method set forth in FIG. 11, a plurality of visual search task stimuli, visual comprehension task stimuli, and verbal comprehension task stimuli are developed. Alternatively, the task stimuli can be selected from a predesigned set of stimuli, such as may be provided as part of a computer software bundle. The method used to develop such stimuli for clinical trials of the inventive method will now be described in detail.

A. Verbal Stimuli

Sixty verbal sentence stimuli were created. Thirty of the stimuli were simple and 30 were complex. Sentence characteristics controlled were: number of words, syllables, propositions, verbs, and word frequency. According to Rochon, Waters, and Caplan (1994) and Thompson and Shapiro (2007) complexity of a sentence can be increased or decreased systematically through careful control and manipulation of these characteristics (except for word frequency). Simple and complex sentences had approximately the same number of words/syllables and the same number of verbs. Finally, simple sentences had a simple subject-verb-object sequence while complex sentences included a center embedded prepositional phrase. See FIG. 12 for a summary of sentence characteristics. A study conducted by Grossman et al. (2000) showed that the difference in processing demands between similar sentence types caused an increase in task demands from single to dual-task processing, and that language comprehension deficits increased in individuals with Parkinson's disease (PD). If participants with PD show vulnerability to increased cognitive demands during dual-task processing of prepositional center embedded phrases, one might also expect to find a complexity effects in individuals with aphasia when presented in single- and in dual-task conditions of varying complexity.

Sentence stimuli were recorded by an adult male native speaker of English in a soundproof booth using a high quality dynamic microphone. Each verbal stimulus was digitized (22 kHz, low-pass filtered at 10.5 kHz), normalized for intensity, and stored on the stimulus presentation computer.

B. Visual Stimuli for Visual Search Task

Figure 13:
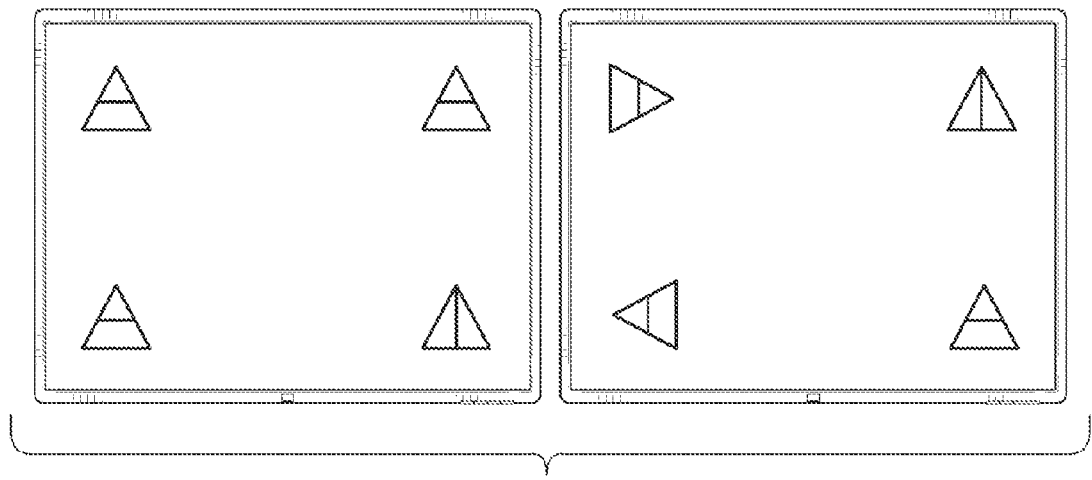
FIG. 13 is an illustration of a sample visual stimulus used in the single-task condition visual search task of the method for testing attention allocation of the present invention.

Sixty multiple-choice displays were created, each including one image in each corner of the display. Three of these images were foil images and one image was a target image that differed in terms of visual complexity from the other images in the display. Thirty simple visual search displays were created, including images in which the three foils were exactly the same and the target was different in terms of complexity. Thirty complex displays were created including three identical foils. Each of these foils had a different orientation, the rationale for which was based on the findings of Shepard and Metzler (1971), who presented eight participants with two visual stimuli at a time consisting of angular forms with varying orientation. The authors asked participants to decide whether the forms were the same shape regardless of their orientation. Results indicated that reaction times increased with an increase in angular disparity of the stimuli. The authors assumed that one has to mentally rotate the objects into the same position before one can compare the stimuli. Thus, mental rotation may increase the cognitive load of the visual search task. See FIG. 13 for an example.

C. Visual Stimuli for Comprehension Task

Figure 14:
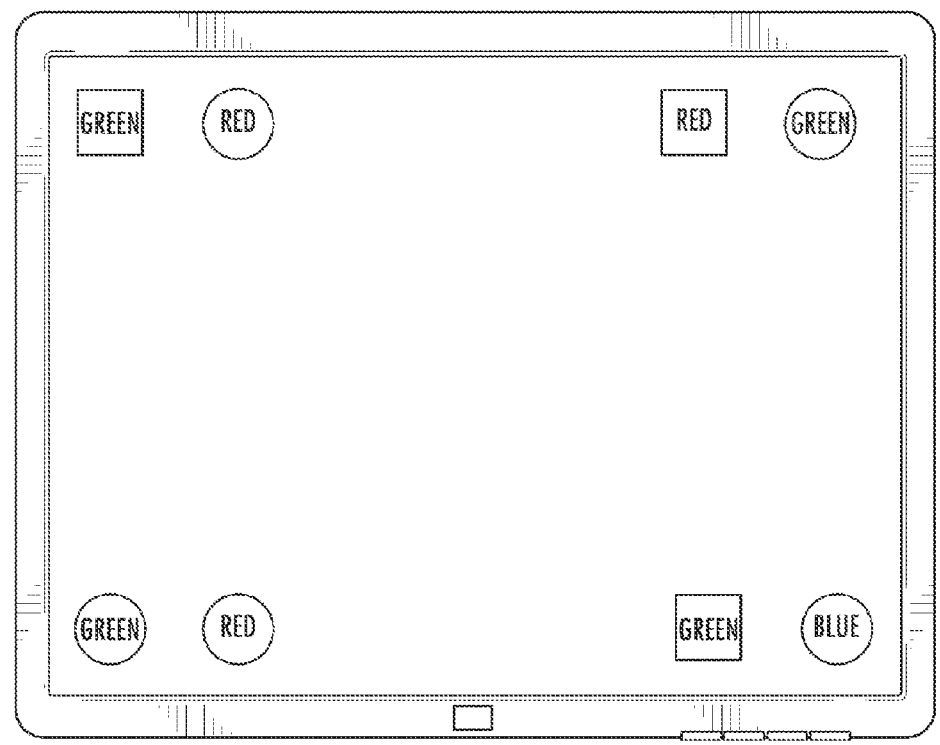
FIG. 14 is an illustration of a sample visual stimulus used in the single-task condition comprehension task of the method for testing attention allocation of the present invention.

Sixty displays containing simple visual stimuli that were controlled in terms of color (red, blue, white and green); size (small and big) and shape (circle and square) were created. The design of these displays was based on research by Hallowell, Wertz and Kruse (2002), showing the feasibility of using similar displays to assess auditory comprehension using eye tracking. In each image two visual stimuli were presented. One image in each display corresponded to the sentence stimulus (the target image) while three images were foils. Their semantic relationship to the target was objectively defined as follows: If the target was "green square and red circle", one foil was "red square and green circle" (reverse of the target), one foil was "green square and blue circle" (one color is wrong), and one foil was green circle and red circle (one shape is wrong). See FIG. 14 for an example (note that the objects shown on the screen in FIG. 14 are displayed to a patient in color, and that the color words in FIG. 14 are provided for the benefit of readers of this black and white text only)

Referring to the next step of the inventive method for assessing the attention allocation of a patient using eye tracking set forth in FIG. 11, the patient to be tested is preferably subjected to vision and hearing screenings in the manner described above under the section titled "Testing Linguistic Comprehension Using Eyetracking." Next, the patient is positioned in front of a computer monitor in a seated position and a conventional eyetracking system is configured to track the patient's eye movements as the patient looks onto the screen of the computer monitor, also as described in the linguistic comprehension section above.

Figure 15:
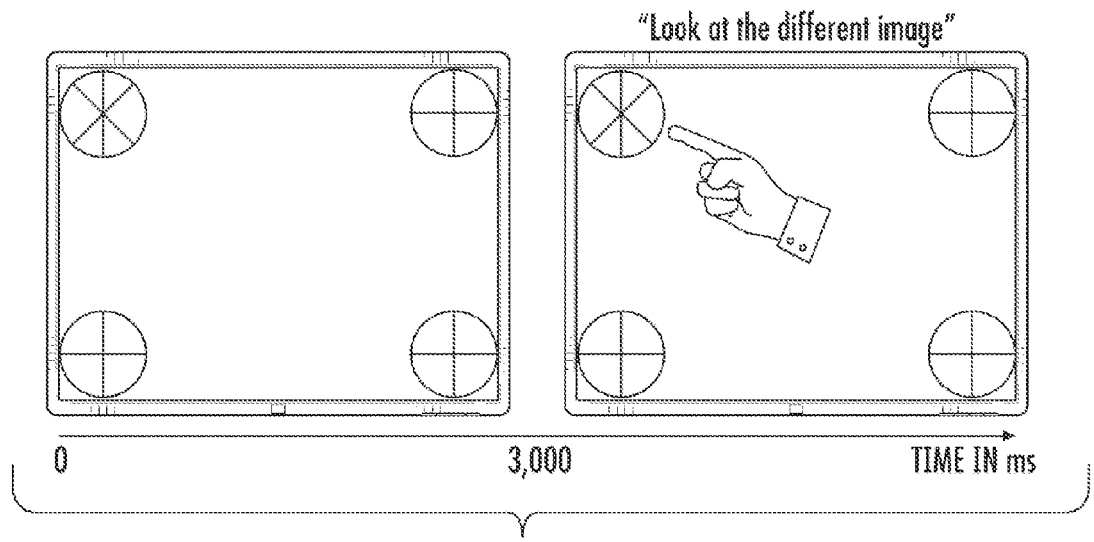
FIG. 15 is an illustration of a sample training sequence for the single-task condition visual search task of the method for testing attention allocation of the present invention.

Next, the patient is preferably subjected to a brief training period for the single visual search task to ensure that the patient understands what he or she is supposed to do during testing. Accordingly, while tracking the patient's eye movements, the patient is presented with a series of multiple-choice image displays on the computer monitor. Each display contains one target image and three foil images that are similar to the images described in the "Visual Stimuli for Visual Search Task" section above. All of the images share a variety of image characteristics (e.g., size, shape, and complexity). In each display the three foil images are identical while the target image differs with respect to one of those image characteristics. Each image display is presented for three seconds to ensure that the patient perceives all images in the display. According to Henderson and Hollingworth (1999), visual features are processed within the first seconds of scene viewing. Thus three seconds are considered to be sufficient for the patient to attend to all images within the display briefly. After three seconds the examiner instructs the participant to "Look at the different image" while the examiner points to the target image. The procedure is summarized in FIG. 15. This procedure is repeated three times so that the patient has been given two examples of simple visual search tasks and two examples of complex visual search tasks.

Next, five simple and five complex practice visual search task trials are presented to the patient. During the practice trials the patient's eye movements are observed on a computer screen by the examiner (see the description of the "clinician display" under the linguistic comprehension assessment section above). The examiner observes and tallies whether the patient fixates on the target images during the visual search task. If the participant chooses a foil instead of a target image, the examiner shows that display again and gives the following feedback: "you looked at this image" (examiner points at the patient's incorrect choice). "This is the different image" (examiner points to the correct target image). If the patient is unable to complete at least three simple and three complex practice trials correctly, he or she is preferably excluded from further testing.

Next, actual testing begins and the single-task condition visual search task is administered to the patient. Accordingly, while tracking the patient's eye movements, the patient is presented with 60 visual search task trials similar to those administered during training for the visual search task, each trial lasting 6000 milliseconds and accompanied by the verbal instruction "look at the different image." In a free viewing scenario, visual processing without presence of any linguistic stimuli has been shown to occur quickly, within the first second of stimulus presentation. Eye-tracking studies on visual stimulus control with individuals without neurogenic impairment have shown that 3000 milliseconds is a sufficient time interval to process similar multiple-choice image displays. Peripheral vision was controlled by presenting the images at a distance of at least 20 degrees of visual angle apart, one in each of the four corners of the screen.

Figure 16:
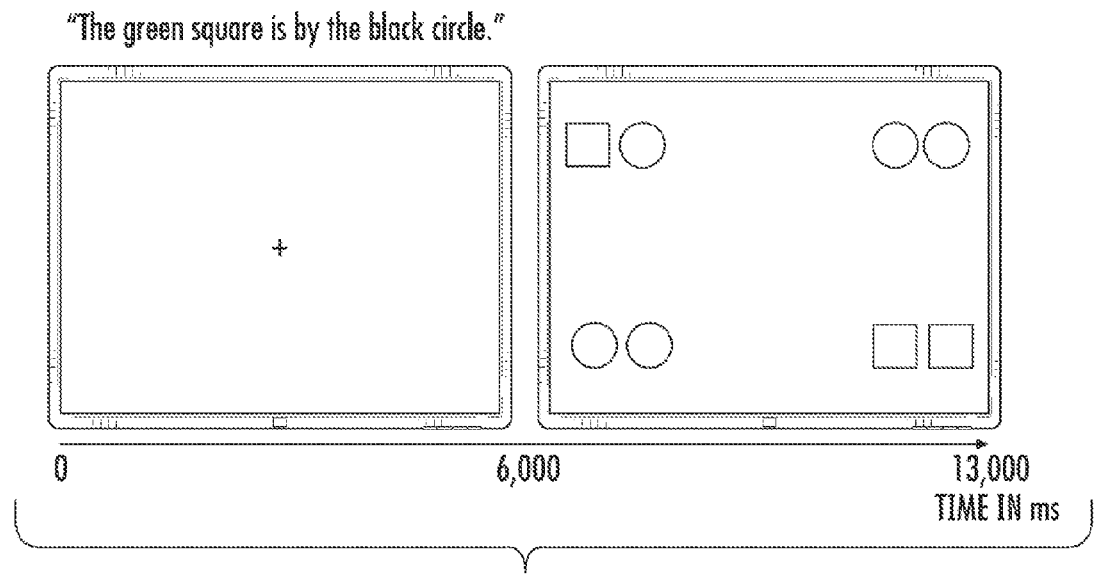
FIG. 16 is an illustration of a sample trial of the single-task condition comprehension task of the method for testing attention allocation of the present invention.

Referring to the next step of the inventive method set forth in FIG. 11, the single-task condition comprehension task is administered to the patient. The patient is first instructed to "listen carefully to the words." Next, while tracking the patient's eye movements, a verbal stimulus similar to the stimuli described in the "Verbal Stimuli" section above is presented to the patient through loudspeakers while the patient is asked to look at a blank computer screen for 6000 milliseconds. A multiple-choice image display containing images similar to those described in the "Visual Stimuli for Comprehension Task" section above is then presented to the patient. Four images are displayed in each of the four corners of the screen. One of the images is a target image that corresponds to the verbal stimulus sentence, and the other three images are foils. This display is preferably presented for twice as long as the verbal stimulus (3000 milliseconds) plus one second, rounded up to the next full second, resulting in a 7000 milliseconds duration. This time span is chosen to ensure that participants have enough time to process the verbal stimulus (potentially rehearsing the verbal stimulus subvocally) and look at the corresponding image display. It is contemplated that the durations can be varied as necessary. A single trial of the comprehension task is presented in FIG. 16.

Figure 17:
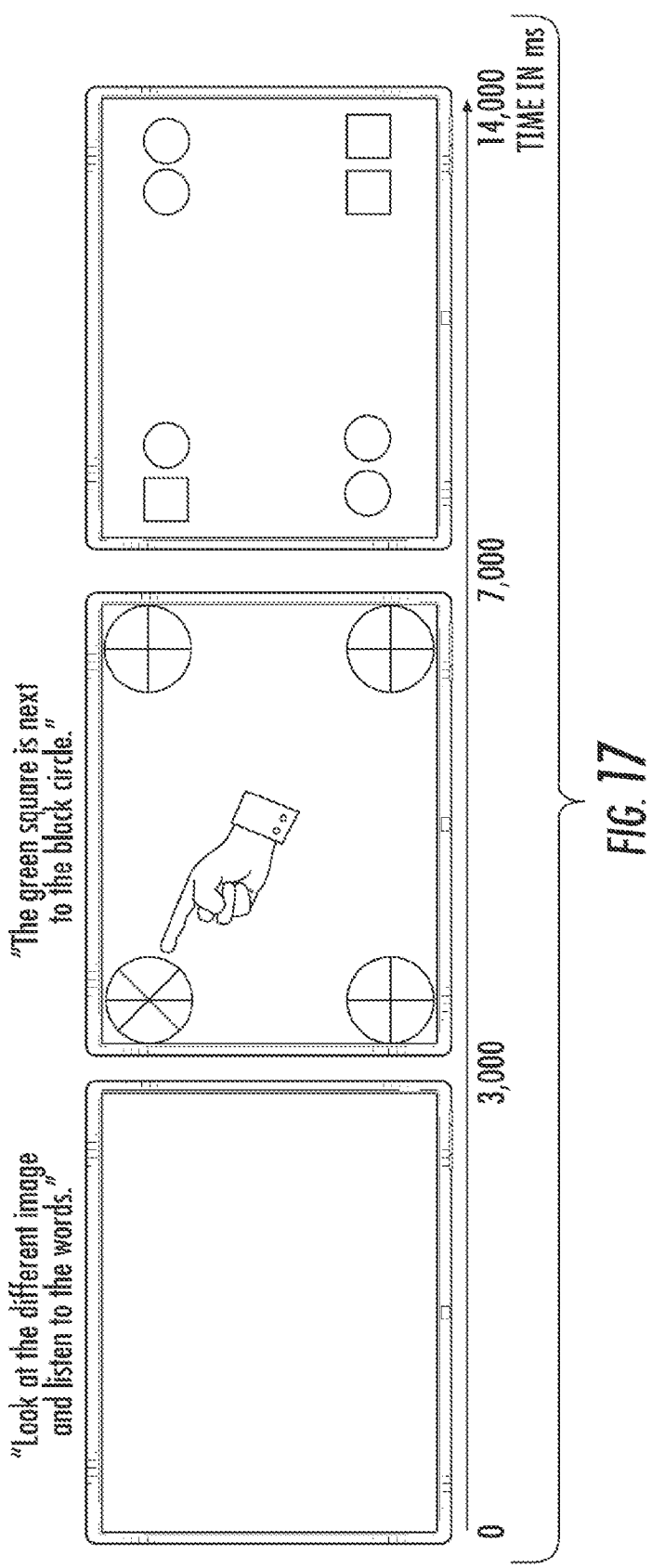
FIG. 17 is an illustration of a sample training sequence for the dual-task condition of the method for testing attention allocation of the present invention.

Next, the patient is preferably subjected to a brief training period for the dual-task condition to ensure that the patient understands what he or she is supposed to do during dual-task testing. Accordingly, while tracking the patient's eye movements, the patient is given the following instruction: "look at the different image and listen carefully to the words." Next, while tracking the patient's eye movements, the patient is presented with the visual search task (described above) and a verbal stimulus (similar to the verbal stimuli described above) simultaneously. After three seconds the examiner points to the target image for the visual search task. A multiple-choice display containing images similar to those described in the "Visual Stimuli for Comprehension Task" section above, one of which is a target image corresponding to the verbal stimulus, is then presented to the patient. This procedure is repeated three times so that the patient is given two examples of simple visual search tasks with simple verbal stimuli and two examples of complex visual search tasks with complex verbal stimuli. See FIG. 17 for an example of the training procedure.

Next, 12 practice trials of the dual-task are presented, including four simple trials (simple auditory and visual stimuli), four complex trials (complex visual and auditory stimuli) and four mixed trials (mixed complexity of visual and linguistic stimuli). If the patient chooses a foil instead of a target image in the visual search display, the examiner gives the following feedback (or some similar variation thereon): "you looked at this image" (examiner points at the patient's incorrect choice). "This is the different image" (examiner points to the correct target image). "Look at the different image." If the patient is unable to complete at least eight of the practice trials correctly, he or she is preferably excluded from further testing.

Eye movements during the dual-task practice trials are observed online on a computer screen by the examiner (see the description of the "clinician display" under the linguistic comprehension assessment section above). The examiner observes and tallies whether patient fixates on the target images during the visual search task in the dual-task condition.

Figure 18:
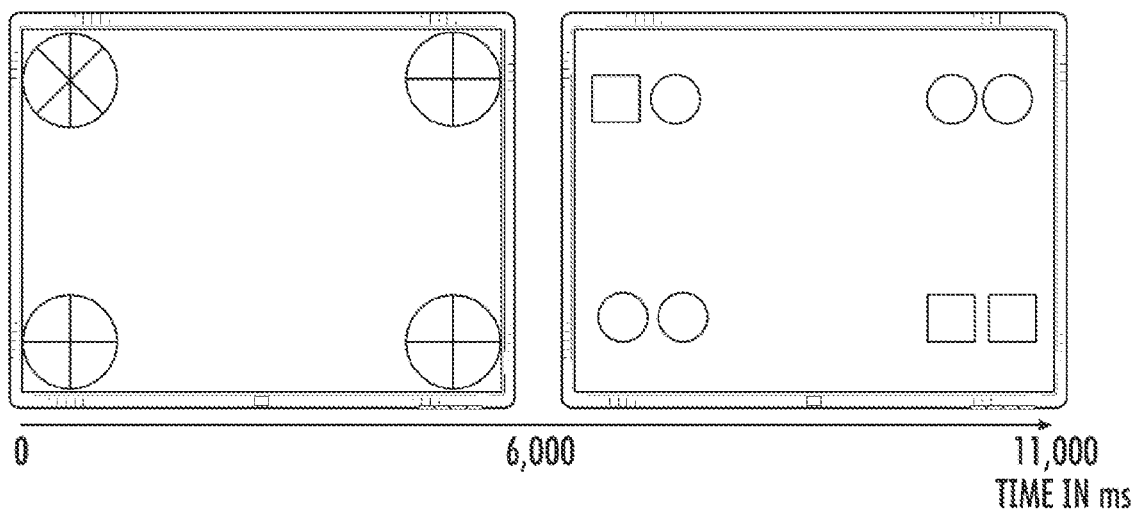
FIG. 18 is an illustration of a sample trial of the dual-task condition of the method for testing attention allocation of the present invention.

Referring to the next step of the inventive method set forth in FIG. 11, a series of dual-task trials is administered to the patient. Accordingly, while tracking the patient's eye movements, the patient is simultaneously presented with the verbal sentence stimuli and the visual search task in the manner described above under the dual task training section. The verbal stimuli each has a duration of 3000 milliseconds. The visual search image display is presented for 6000 milliseconds followed immediately by the second multiple-choice image display, with the target image corresponding to the auditory stimulus. This display is presented for 7000 milliseconds, twice as long as the verbal stimulus plus one second, based on Hallowell et al., (2002). See FIG. 18 for an example of the dual-task condition.

A patient's eye-fixation duration measures during administration of the above-described method steps have been found to be a reliable indicator of the patient's ability to effectively allocate attention resources. Such measures include the proportion of fixation duration (the total duration for which an individual fixates on one specific area divided by the total time of all fixations during the viewing of a display), average fixation duration (the mean fixation duration for all fixations on a particular item in the display), and first-pass fixation duration on a target (the time interval between when a viewer first fixates on and first fixates away from an area of interest). Specifically, a greater decrease in the duration of such measures when comparing a patient's performance in the dual-task condition to his or her performance in the single-task condition correlates with a greater deficiency in the patient's ability to allocate attention resources.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A method for obtaining eye-fixation duration data or eye-fixation duration and location data for assessing a patient's linguistic comprehension using an eyetracking system comprising at least one video camera and at least one computer that is configured to measure and record the patient's eye-fixation data, the method comprising:
   a. presenting the patient with a verbal stimulus;
   b. presenting the patient with a visual stimulus comprising a plurality of images wherein one of the images is a target image that corresponds to the verbal stimulus;
   c. measuring and recording eye-fixation duration data during steps a and b, wherein an eye fixation is a relatively stable position of the eye for a minimum duration of at least about 40 milliseconds with some slight tolerance in the vertical and horizontal dimensions; and
   d. analyzing the eye-fixation duration data to assess the patient's linguistic comprehension.

2. The method in accordance with claim 1, wherein the verbal stimulus is presented audibly.

3. The method in accordance with claim 2, wherein the verbal stimulus is prerecorded.

4. The method in accordance with claim 1, wherein the verbal stimulus is presented textually.

5. The method in accordance with claim 1, wherein the visual stimulus is presented on a computer screen.

6. The method in accordance with claim 1, further comprising interpreting the eye-fixation duration data in relation to normative data.

7. The method in accordance with claim 1, further comprising designing the visual stimulus to minimize the presence of distracting visual features.

8. The method in accordance with claim 1, further comprising administering a hearing screening prior to presenting the patient with stimuli.

9. The method in accordance with claim 1, further comprising administering a vision screening prior to presenting the patient with stimuli.

10. The method in accordance with claim 1, further comprising administering practice trials of the method.

11. A method for obtaining eye-fixation duration data or eye-fixation duration and location data for assessing the effect of semantic associative priming on a patient using an eye-tracking system comprising at least one video camera and at least one computer that is configured to measure and record the patient's eye-fixation data, the method comprising:
    a. presenting the patient with a prime word;
    b. presenting the patient with a visual stimulus comprising a plurality of images wherein one of the images is a target image that has a high semantic association with the prime word;
    c. measuring and recording eye-fixation duration data during steps a and b, wherein an eye fixation is a relatively stable position of the eye for a minimum duration of at least about 40 milliseconds with some slight tolerance in the vertical and horizontal dimensions; and
    d. analyzing the eye-fixation duration data to assess the effect of semantic associative priming on the patient.

12. The method in accordance with claim 11, wherein the prime word is presented audibly.

13. The method in accordance with claim 12, wherein the prime word is prerecorded.

14. The method in accordance with claim 11, wherein the prime word is presented textually.

15. The method in accordance with claim 11, wherein the visual stimulus is presented on a computer screen.

16. The method in accordance with claim 11, further comprising interpreting the eye-fixation duration data in relation to normative data.

17. The method in accordance with claim 11, further comprising designing the visual stimulus to minimize the presence of distracting visual features.

18. The method in accordance with claim 11, further comprising administering a hearing screening prior to presenting the patient with stimuli.

19. The method in accordance with claim 11, further comprising administering a vision screening prior to presenting the patient with stimuli.

20. The method in accordance with claim 11, further comprising administering practice trials of the method.

21. A method for obtaining eye-fixation duration data or eye-fixation duration and location data for testing the working memory of a patient using an eyetracking system comprising at least one video camera and at least one computer that is configured to measure and record the patient's eye-fixation data, the method comprising:
    a. presenting the patient with a verbal stimulus;
    b. presenting the patient with a first visual stimulus comprising a plurality of images wherein one of the images is a target image that corresponds to the verbal stimulus;

c. presenting the patient with a second visual stimulus comprising an image to be remembered;
d. presenting the patient with a recognition display comprising a plurality of images wherein one of the images corresponds to the second visual stimulus;
e. measuring and recording eye-fixation duration data during steps a to d, wherein an eye fixation is a relatively stable position of the eye for a minimum duration of at least about 40 milliseconds with some slight tolerance in the vertical and horizontal dimensions; and
f. analyzing the eye-fixation duration data to assess the patient's working memory.

22. The method in accordance with claim 21, wherein the verbal stimulus is presented audibly.

23. The method in accordance with claim 22, wherein the verbal stimulus is prerecorded.

24. The method in accordance with claim 21, wherein the verbal stimulus is presented textually.

25. The method in accordance with claim 21, wherein the visual stimuli are presented on a computer screen.

26. The method in accordance with claim 21, further comprising interpreting the eye-fixation duration data in relation to normative data.

27. The method in accordance with claim 21, further comprising designing the first visual stimulus to minimize the presence of distracting visual features.

28. The method in accordance with claim 21, further comprising administering a hearing screening prior to presenting the patient with stimuli.

29. The method in accordance with claim 21, further comprising administering a vision screening prior to presenting the patient with stimuli.

30. The method in accordance with claim 21, further comprising administering practice trials of the method.

31. A method for obtaining eye-fixation duration data or eye-fixation duration and location data for testing the attention allocation of a patient using an eyetracking system comprising at least one video camera and at least one computer that is configured to measure and record the patient's eye-fixation data, the method comprising:
   a. administering a single-task condition visual search task comprising:
      i. presenting the patient with a first multiple choice display containing a plurality of images wherein all of the images are identical except for a first target image that is different with respect to at least one image characteristic; and
      ii. instructing the patient to look at the different image;
   b. administering a single-task condition comprehension task comprising:
      i. presenting the patient with a first verbal stimulus; and
      ii. presenting the patient with a first visual stimulus comprising a plurality of images wherein one of the images is a second target image that corresponds to the first verbal stimulus;
   c. administering a dual-task comprising:
      i. instructing the patient to look at the different image and listen carefully to the words;
      ii. simultaneously presenting the patient with a second verbal stimulus and a second multiple choice display containing a plurality of images wherein all of the images are identical except for a third target image that is different with respect to at least one image characteristic; and
      iii. presenting the patient with a second visual stimulus comprising a plurality of images wherein one of the images is a forth target image that corresponds to the second verbal stimulus;
   d. measuring and recording eye-fixation duration data during steps a to c, wherein an eye fixation is a relatively stable position of the eye for a minimum duration of at least about 40 milliseconds with some slight tolerance in the vertical and horizontal dimensions; and
   e. analyzing the eye-fixation duration data to assess the patient's attention allocation.

32. The method in accordance with claim 31, wherein the verbal stimuli are presented audibly.

33. The method in accordance with claim 32, wherein the verbal stimuli are prerecorded.

34. The method in accordance with claim 31, wherein the verbal stimuli are presented textually.

35. The method in accordance with claim 31, wherein the visual stimuli are presented on a computer screen.

36. The method in accordance with claim 31, further comprising interpreting the eye-fixation duration data in relation to normative data.

37. The method in accordance with claim 31, further comprising designing the visual stimuli to minimize the presence of distracting visual features.

38. The method in accordance with claim 31, further comprising administering a hearing screening prior to presenting the patient with stimuli.

39. The method in accordance with claim 31, further comprising administering a vision screening prior to presenting the patient with stimuli.

40. The method in accordance with claim 31, further comprising administering training for the single-task condition visual search task.

41. The method in accordance with claim 31, further comprising administering training for the single-task condition comprehension task.

42. The method in accordance with claim 31, further comprising administering training for the dual-task.

43. The method in accordance with claim 1, wherein the eye fixation has a minimum duration in the range of about 40 milliseconds to about 250 milliseconds.

44. The method in accordance with claim 1, wherein the eye fixation has a minimum duration of at least about 100 milliseconds.

45. The method in accordance with claim 11, wherein the eye fixation has a minimum duration in the range of about 40 milliseconds to about 250 milliseconds.

46. The method in accordance with claim 11, wherein the eye fixation has a minimum duration of at least about 100 milliseconds.

47. The method in accordance with claim 21, wherein the eye fixation has a minimum duration in the range of about 40 milliseconds to about 250 milliseconds.

48. The method in accordance with claim 21, wherein the eye fixation has a minimum duration of at least about 100 milliseconds.

49. The method in accordance with claim 31, wherein the eye fixation has a minimum duration in the range of about 40 milliseconds to about 250 milliseconds.

50. The method in accordance with claim 31, wherein the eye fixation has a minimum duration of at least about 100 milliseconds.

* * * * *

UNITED STATES PATENT AND TRADEMARK OFFICE
CERTIFICATE OF CORRECTION

PATENT NO. : 8,602,789 B2
APPLICATION NO. : 12/579154
DATED : December 10, 2013
INVENTOR(S) : Brooke Hallowell and Hans Kruse It is certified that error appears in the above-identified patent and that said Letters Patent is hereby corrected as shown below:

In the specification

Prior to Column 1, line 4, insert the following:

--STATEMENT OF GOVERNMENT INTEREST

This invention was made with government support under K23DC001530 awarded by National Institute of Health. The government has certain rights in the invention.--

Signed and Sealed this
First Day of November, 2016

Michelle K. Lee
*Director of the United States Patent and Trademark Office*